US010649019B2

(12) United States Patent
Schubert et al.

(10) Patent No.: US 10,649,019 B2
(45) Date of Patent: May 12, 2020

(54) OPTICALLY PROBED MULTI-ELEMENT ELECTRIC FIELD SENSING SYSTEM

(71) Applicant: X Development LLC, Mountain View, CA (US)

(72) Inventors: Martin Friedrich Schubert, Mountain View, CA (US); Michael Jason Grundmann, San Jose, CA (US)

(73) Assignee: X Development LLC, Mountain View, CA (US)

( * ) Notice: Subject to any disclaimer, the term of this patent is extended or adjusted under 35 U.S.C. 154(b) by 131 days.

(21) Appl. No.: 15/694,739

(22) Filed: Sep. 1, 2017

(65) Prior Publication Data

US 2019/0072599 A1     Mar. 7, 2019

(51) Int. Cl.
*G01R 29/08*     (2006.01)
*A61B 5/0476*    (2006.01)
(Continued)

(52) U.S. Cl.
CPC ........ *G01R 29/0885* (2013.01); *A61B 5/0022* (2013.01); *A61B 5/0082* (2013.01); *A61B 5/0476* (2013.01); *A61B 5/0478* (2013.01); *A61B 5/1495* (2013.01); *A61B 5/14553* (2013.01); *A61B 2562/046* (2013.01)

(58) Field of Classification Search
CPC ................................................. G01R 29/0885
See application file for complete search history.

(56) References Cited

U.S. PATENT DOCUMENTS

| 4,367,040 A | 1/1983 | Goto |
| 4,775,214 A | 10/1988 | Johnson |

(Continued)

FOREIGN PATENT DOCUMENTS

EP     0997738     6/2003

OTHER PUBLICATIONS

'journals.plos.org' [online] "Electric Field Encephalography as a Tool for Functional Brain Research: A Modeling Study," Yury Petrov, Jul. 2, 2013, [retrieved on Dec. 5, 2017] Retrieved from Internet: URL< http://journals.plos.org/plosone/article?id=10.1371/journal.pone.0067692> 9 pages.

(Continued)

*Primary Examiner* — Noam Reisner
(74) *Attorney, Agent, or Firm* — Fish & Richardson P.C.

(57) ABSTRACT

A system and a method for determining local electric field strengths, the system including: a light source module configured to emit light; a plurality of electric field sensors, each sensor including a light input portion and a light output portion, each sensor including an electro-optic material arranged in a path of at least some of the received light, an optical property of the electro-optic material being variable depending on a local electric field strength at the sensor, and the electro-optic material being arranged in the sensor such that a property of the output light varies depending on the local electric field strength; a light detection module arranged to receive the output light from the sensors; and a processing module in communication with the light detection module, the processing module being programmed to determine a corresponding value for the electric field strength local to each of the sensors.

26 Claims, 13 Drawing Sheets

(51) Int. Cl.
*A61B 5/00* (2006.01)
*A61B 5/1495* (2006.01)
*A61B 5/1455* (2006.01)
*A61B 5/0478* (2006.01)

(56) References Cited

U.S. PATENT DOCUMENTS

| | | | |
|---|---|---|---|
| 5,041,779 A * | 8/1991 | Hales | G01R 29/0885 324/96 |
| 5,097,476 A | 3/1992 | Thiessen | |
| 5,177,805 A | 1/1993 | Groger et al. | |
| 5,267,336 A | 11/1993 | Sritam et al. | |
| 5,280,173 A | 1/1994 | Morse et al. | |
| 5,379,309 A | 1/1995 | Logan, Jr. | |
| 5,513,913 A | 5/1996 | Ball et al. | |
| 5,583,637 A | 12/1996 | Tokano et al. | |
| 5,835,458 A * | 11/1998 | Bischel | G11B 7/122 369/44.12 |
| 5,952,818 A | 9/1999 | Zhang et al. | |
| 5,963,034 A | 10/1999 | Mahapatra et al. | |
| 6,111,416 A | 8/2000 | Zhang et al. | |
| 6,901,101 B2 | 5/2005 | Frick | |
| 8,896,302 B1 | 11/2014 | Zhu et al. | |
| 10,038,301 B1 | 7/2018 | Eggleston | |
| 2004/0233458 A1 | 11/2004 | Frick | |
| 2009/0135870 A1 | 5/2009 | Hayat | |
| 2010/0264904 A1 * | 10/2010 | Wu | G01R 29/0885 324/97 |
| 2011/0277540 A1 | 11/2011 | Ioppolo et al. | |
| 2012/0086443 A1 | 4/2012 | Bazzone | |
| 2014/0368201 A1 * | 12/2014 | Leblanc | G01V 3/26 324/339 |
| 2016/0120432 A1 * | 5/2016 | Sridhar | A61B 5/6898 600/544 |
| 2017/0264070 A1 | 9/2017 | Cingoz | |
| 2018/0115135 A1 | 4/2018 | Hu | |
| 2019/0072600 A1 | 3/2019 | Schubert | |

OTHER PUBLICATIONS

Koo et al. "Bragg grating-based laser sensors systems with interferometric interrogation and wavelength division multiplexing," Journal of Lightwave Technology, vol. 13(7), Jul. 1995, 7 pages.

Lee et al. "Ultra-low-loss optical delay line on a silicon chip" Nature Communications 3(867), May 29, 2012, 7 pages.

Parker et al. "Monolithically Integrated Gain-Flattened Ring Mode-Locked Laser for Comb-Line Generation," IEEE Photonics Technology Letters 24.2, Jan. 15, 2012, 3 pages.

U.S. Non-final Office Action in U.S. Appl. No. 15/694,743, dated May 10, 2019, 19 pages.

\* cited by examiner

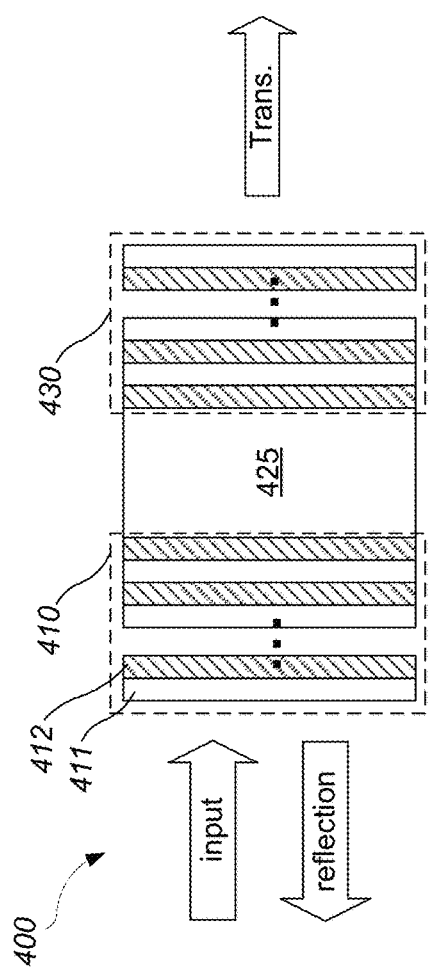
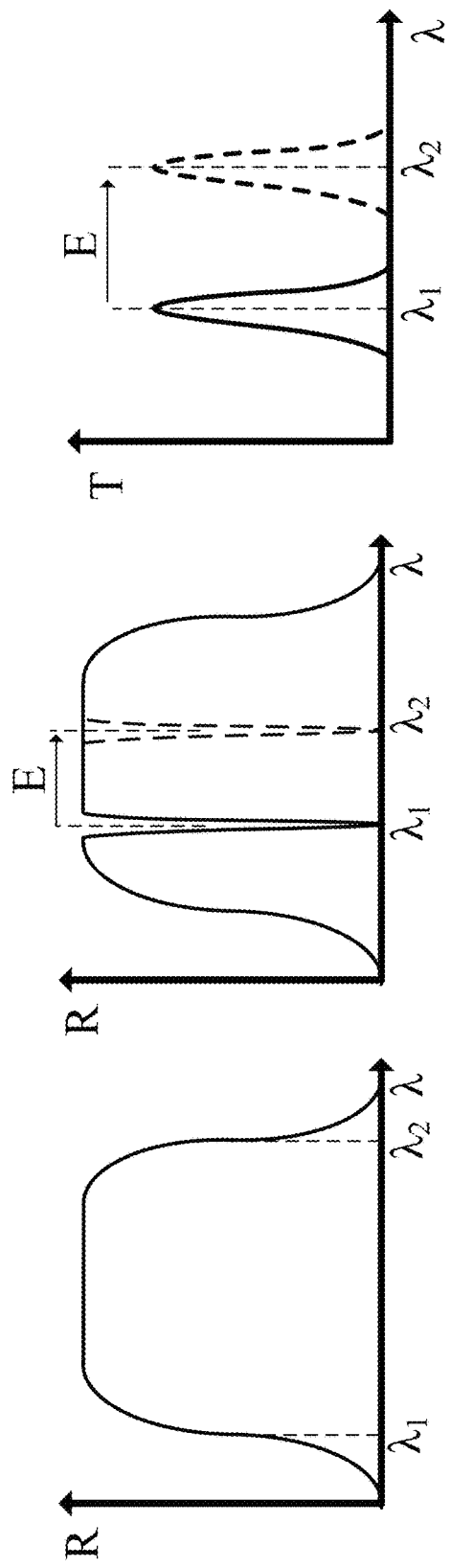
FIG. 4A
FIG. 4B
FIG. 4C
FIG. 4D

OPTICALLY PROBED MULTI-ELEMENT ELECTRIC FIELD SENSING SYSTEM

TECHNICAL FIELD

This disclosure generally relates to electric field sensing devices, systems, and methods of measuring the electric field using the sensing devices and systems.

BACKGROUND

An electric field is a vector quantity of electric potential gradient at a point in space, and may be measured in unit of volts per meter. Electric field can be generated in various ways such as by a presence of charged particles and movement of the charged particles. Electric field can be measured in various ways. For example, two parallel conducting plates, e.g., a parallel plate capacitor, can be used to measure a local electric field strength. As another example, sensors based on silver/silver chloride electrodes can be used to measure the local electric field strength.

An Electro-Optic (EO) material is material that changes an optical property, such as refractive index and/or absorption coefficient, in response to a local electric field. Some EO materials exhibit a proportional (e.g., linear) change in refractive index as a function of the local electric field, at least over a range of electric field strengths. Examples of such EO materials include Lithium Niobate.

SUMMARY

This disclosure features architectures for sensitive detection of local electric field strengths at multiple locations using an optical probe. In certain implementations, the system incorporates an optically-probed sensor that operate in transmission and/or in reflection mode by imparting a change in an amplitude or a spectrum of probe light in response to the electric field strength local to each sensor. In certain implementations, the optically-probed sensors can include additional sensitivity-enhancing elements including an optical gain medium, a saturable absorber, and/or a plasmonic waveguide.

Implementations can be used in various applications involving spatial mapping of local electric fields. Examples of such applications include brain-wave monitoring, large-area phased array receivers, radar detection, oceanographic studies, and geospatial prospecting. Furthermore, the system may be operated in restricted environments such as environments with electric shock hazards or high magnetic fields due to electromagnetic isolation provided by use of an optical probe.

In general, in a first aspect, the invention features a system that includes: a light source module configured to emit light; a plurality of electric field sensors, each sensor including a light input portion configured to receive light emitted from the light source module and a light output portion configured to output light in response to the received light, each sensor including an electro-optic material arranged in a path of at least some of the received light, an optical property of the electro-optic material being variable depending on a local electric field strength at the sensor, and the electro-optic material being arranged in the sensor such that a property of the output light varies depending on the local electric field strength; a light detection module arranged to receive the output light from the sensors; and a processing module in communication with the light detection module, the processing module being programmed to determine a corresponding value for the electric field strength local to each of the sensors based on the detected output light from each respective sensor.

Embodiments of the system can include one or more of the following features. For example, the light emitted by the light source module can include a plurality of wavelengths; and the plurality of electric field sensors can be responsive to one or more corresponding wavelengths of the plurality of wavelengths. As another example, the light emitted by the light source module can include a plurality of wavelengths and the plurality of electric field sensors can each have a respective resonant wavelength which vary depending on the electric field strength local to the respective electric field sensor.

The light detection module can be configured to separately detect light at each of the corresponding one or more of the plurality of wavelengths.

The processing module can be programmed to determine corresponding local electric field strength at each of the sensors based on the detected wavelengths of light corresponding to each sensor.

The common optical path can include an optical waveguide.

Each of the plurality of electric field sensors can include a multiplexer and a demultiplexer.

In some embodiments, the plurality of electric field sensors are arranged at different locations along a common optical path of the light from the light source module. Various examples of the electric field sensors include a ring resonator, a fiber grating, a distributed Bragg reflector defect cavity, an optical delay line, and a photonic crystal cavity.

In some embodiments, the system can include an optical circulator optically coupled to the light source module, the plurality of electric field sensors, and the light detection module.

In some embodiments, the light source module emits optical pulses during operation and the processing module is programmed to correlate each of a plurality of detected optical pulses to a corresponding electric field sensor based on a respective arrival time of the detected optical pulse.

In some embodiments, the system can further include an optical circulator optically coupled to the light source module, the plurality of electric field sensors, and the light detection module.

In some embodiments, the light emitted by the light source module includes a plurality of wavelengths, and the plurality of electric field sensors includes a plurality of retroreflectors configured to retroreflect the light received by the plurality of electric field sensors, the plurality of electric field sensors each having a respective resonant wavelength which vary depending on the electric field strength local to the respective electric field sensor.

In a system including a plurality of retroreflectors, the retroreflector can be a cube corner retroreflector. Additionally, the electro-optic material can be integrated with the cube corner to form a reflective surface of the cube corner.

In some embodiments, each of the plurality of electric field sensors can include an optical gain medium, a saturable absorber, a plasmonic waveguide, or a combination thereof.

In some embodiments, the light emitted by the light source module includes a pump wavelength and a plurality of probe wavelengths, and the plurality of electric field sensors can be responsive to one or more corresponding wavelengths of the plurality of probe wavelengths. In such embodiments, each of the plurality of electric field sensors can include an optical gain medium arranged in a path of at least some of the received light, and the optical gain medium can have an optical gain that vary depending on an amount of received pump light. Additionally, in such embodiments, the electro-optic material can be configured to transmit a variable portion of the pump wavelength to the optical gain medium depending on the electric field strength local to the respective electric field sensor, such that respective intensity of the output probe wavelengths are modified by the optical gain of the respective optical gain medium.

Examples of the electro-optic material include lithium niobate, lithium tantalate, potassium di-deuterium phosphate, β-barium borate, potassium titanium oxide phosphate, gallium arsenide, indium phosphide, transition metal dichalcogenides, and poled electro-optic polymers.

The plurality of electric field sensor can be arranged to form a grid.

A wavelength of the emitted light can be in a range from 250 nm to 5,000 nm.

The light source module can be a white light source.

In another aspect, the invention features a method for determining local electric field strengths using optical electric field sensors having an electro-optic material, the method including: illuminating the optical electric field sensors with a light source while the optical electric field sensors are arranged relative to a source of a spatially-varying electric field; detecting output light from each of the optical electric field sensors in response to the illumination, wherein a property of the output light varies depending on the electric field strength local to each respective one of the optical electric field sensors; and determining a corresponding value for the electric field strength local to each of the sensors based on the detected output light from each respective sensor.

Implementations of the method can be implemented using a light source module or electro-optic sensor of other aspects.

In a further aspect, the invention features an electro-optic (EO) sensor for detecting a local electric field strength, the EO sensor including: a first optical cavity;

a gain medium within the first optical cavity; a mode locking element within the first optical cavity; and an EO material within the first optical cavity, an effective optical path length of the EO material being variable depending on the local electric field strength at the EO sensor, wherein the gain medium, the mode locking element, and the EO material are arranged in a common path of light within the first optical cavity, and wherein during operation, the EO sensor emits pulses of light at a repetition rate characteristic of an effective optical path length of the light within the first optical cavity, the effective optical path length varying depending on the electric field strength local to the EO sensor.

Embodiments of the EO sensor can include one or more of the following features and/or features of other aspects. For example, the EO sensor can further include a second optical cavity different from the first optical cavity, wherein the EO material is arranged within the second optical cavity, and the second optical cavity is configured to resonantly enhance a change in the effective optical path length of the light in response to the local electric field strength. Various examples of the second optical cavity can include a distributed Bragg reflector defect cavity, a photonic crystal cavity, a ring resonator, and a fiber grating.

In some embodiments, the gain medium includes a III-V semiconductor, a single quantum well structure, a multiple quantum wells structure, a II-VI semiconductor, a quantum wire, quantum dots, or a combination thereof.

In some embodiments, the mode locking element and a reflector of the optical cavity is provided by a semiconductor saturable absorber mirror.

In some embodiments, the optical cavity, the gain medium, the mode locking element, and the EO material are supported by a common substrate, the common path of light provided by an optical waveguide supported by the common substrate. Various examples of the mode locking element include a graphene-based saturable absorber waveguide, a reverse-biased gain medium. Additionally, in some embodiments, the EO sensor includes a reference mode-locked laser (MLL) supported by the common substrate, the reference MLL including: a third optical cavity; a second gain medium within the third optical cavity; and a second mode locking element within the third optical cavity, wherein the second gain medium and the second mode locking element are arranged in a second common path of light within the third optical cavity, and wherein during operation, the reference MLL emits pulses of light at a reference repetition rate characteristic of a reference effective optical path length of the light within the third optical cavity, the reference effective optical path length invariant to the electric field strength local to the EO sensor.

The reference MLL can be arranged in close proximity the EO sensor. The reference MLL can be placed in close proximity to the EO sensor such that both sensors experience substantially identical environmental variations.

In some embodiments, the common path of light is provided by an optical fiber. In such embodiments, the gain medium can be a rare-earth-doped fiber (e.g., an erbium doped fiber, an ytterbium-doped fiber, a neodymium doped fiber, a thulium doped fiber, and a praseodymium doped fiber).

A wavelength of the emitted pulses of light can be in a range from 250 nm to 5,000 nm.

In another aspect, the invention features a method for determining a local electric field strength using an electro-optic (EO) sensor emitting pulses of light at a repetition rate that vary depending on the local electric field strength, the method including: pumping a gain medium of the EO sensor; detecting the pulses of light emitted by the EO sensor; determining the repetition rate of the pulses of light; and determining the local electric field strength based on the repetition rate.

Implementations of the method can include one or more of the following features and/or features of other aspects. The pumping of the gain medium can include optically pumping the gain medium using a pump light. Alternatively, the pumping of the gain medium can include electrically pumping the gain medium using an electrical current.

In some embodiments, the method for determining a local field strength using an electro-optic (EO) sensor emitting pulses of light at a repetition rate that vary depending on the local electric field strength can include: determining a zero-field repetition rate of the pulses of light; and determining a difference between the repetition rate of the EO sensor and the zero-field repetition rate, wherein the determining of the local electric field strength comprises determining the local electric field strength based on the difference between the repetition rate and the zero-field repetition rate of the EO sensor.

In some embodiments, the method for determining a local field strength using an electro-optic (EO) sensor emitting pulses of light at a repetition rate that vary depending on the local electric field strength can include: determining a reference repetition rate of a reference mode-locked laser (MLL), the reference repetition rate substantially equal to the repetition rate of the EO sensor at zero local electric field strength and invariant to an ambient electric field strength; and determining a difference between the repetition rate of the EO sensor and the reference repetition rate, wherein the determining of the local electric field strength comprise determining the local electric field strength based on the difference between the repetition rate of the EO sensor and the reference repetition rate of the reference MLL.

The determining of the repetition rate of the pulses of light can include one of frequency counting via a frequency counter or spectrum analysis via a spectrum analyzer.

Implementations of the system can include one or more of the following features. For example, the optically-probed sensors can spectrally encode a local electric field strength on the optical probe light by transmitting or reflecting a band of wavelengths of a broadband illumination. A peak or local minimum in the transmitted or reflected wavelengths can be measured to determine the local electric field strength.

Among other advantages, implementations of the optically-probed multi-element electric-field sensing system can provide a low-noise, high-sensitivity electric-field sensing system.

Advantageously, the disclosed system architectures are achievable using optical fibers as an optical channel, enabling flexible form-factors and distributed sensing systems over a large area.

Use of light as a probe to measure a local electric field strength can mitigate some sources of measurement inaccuracies and difficulties associated with electric field measurement using certain conventional methods. For example, many conventional electric field sensors utilize conductive objects, which can distort a local electric field due to interaction of free electrons and holes of the conductive object with the ambient electric field. Accordingly, an electric potential difference generated across the conductive object can generate an unwanted electric field, e.g., Electromagnetic interference (EMI), that can corrupt sensitive measurements of electric fields. Certain conductive objects can also act as an antenna to ambient electric fields, collecting electric fields from points other than a specific point of interest being measured, which can reduce the locality of the electric field measurement and can increase crosstalk in case of multi-point electric field measurements.

In contrast to conductive objects and current flow associated with electrical methods, light does not ordinarily generate EMI, and light can be propagated in free space or in a non-conductive material such as an optical fiber, reducing any possible disturbance to the local electric field being measured. Furthermore, a sensitivity of the electric field measurement using light can potentially be increased through various optical techniques, which can lead to improved signal-to-noise ratio.

The details of one or more implementations of the subject matter of this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 4A shows an electric field sensor including an optical cavity;

FIG. 4B shows an example of a reflection spectrum of a distributed Bragg reflector;

FIG. 4C shows an example of a reflection spectrum of the sensor shown in FIG. 4A;

FIG. 4D shows an example of a transmission spectrum of the sensor shown in FIG. 4A;

Like reference numbers and designations in the various drawings indicate like elements.

DETAILED DESCRIPTION

Optically probed multi-element electric field sensing systems can be used for Electric Field Encephalography (EFEG), which is a study of electric fields generated by the brain. Unlike Electro-Encephalography (EEG), which measures electric potentials across various locations across the scalp through physical contact, EFEG can be performed without physical contact with the scalp as it measures the electric fields instead of the electric potential.

Figure 1:
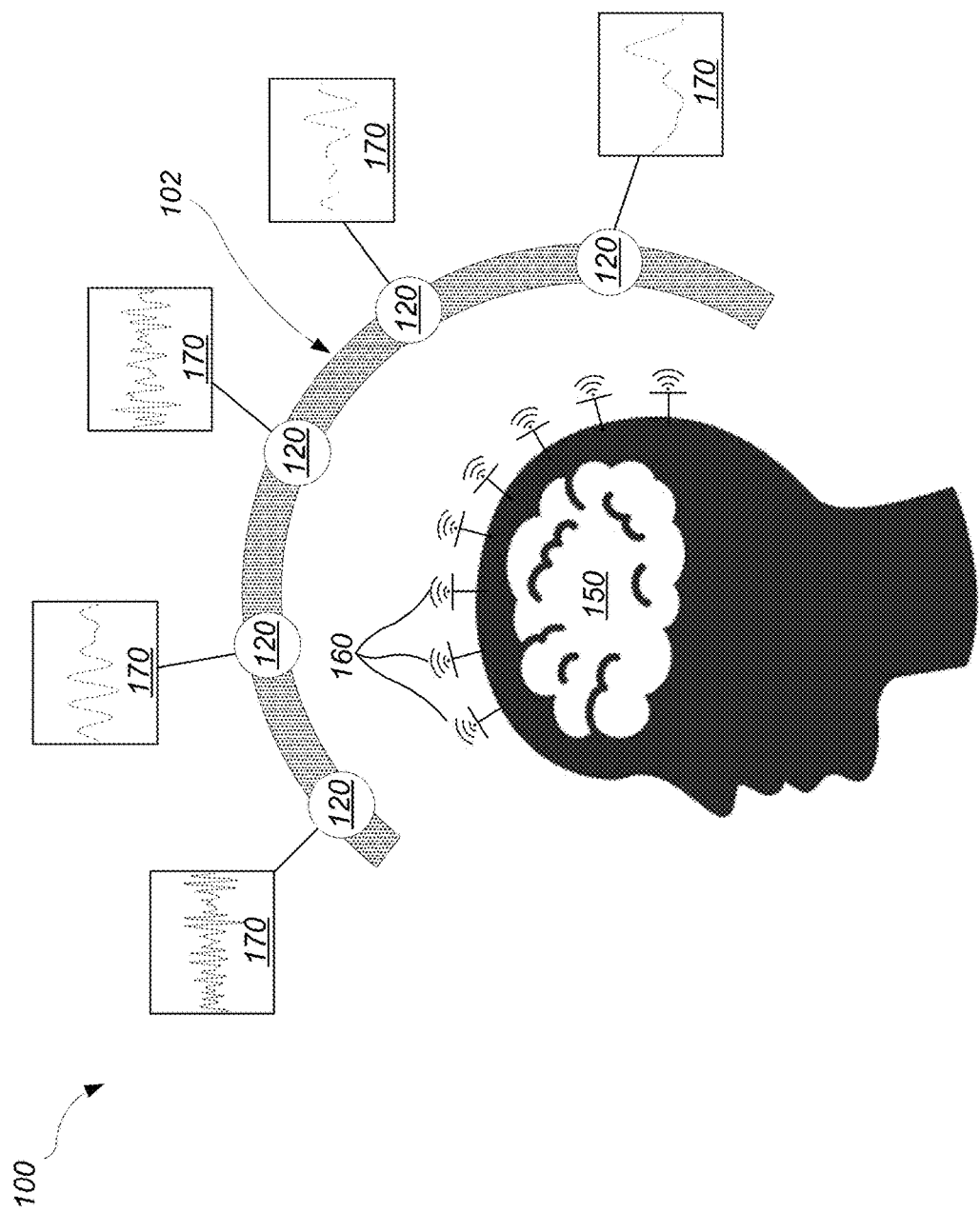
FIG. 1 shows an example of an electric field encephalography system for measuring brain activity.

Referring to FIG. 1, an example of an electric field encephalography system 100 for measuring brain activity is shown. The EFEG system 100 includes an optically probed multi-element electric field sensor 102 that includes multiple electric field sensors 120 that are optically probed. The electric field sensing system 102 is used to perform EFEG on a brain 150. Some approaches to studying the electric fields generated by the brain 150 utilizes multiple current dipoles 160 placed across various locations throughout the brain 150 as modeling elements. Electromagnetic waves emitted by the current dipoles 160 each contribute to respective local electric fields 170 at the locations of the electric field sensors 120.

In the context of EFEG, the brain 150 may be modeled, for example, using an anisotropic 4-shell spherical head model or a 3-shell boundary element method (BEM) model. In such models, current dipoles 160 may be used as modeling elements that are distributed inside and on the surface of the brain 150. Such current dipoles 160 serve as proxies for corresponding portions of the brain 150, serving as points of origin, or sources, of electromagnetic waves generated by the corresponding portions of the brain 150. In general, current dipoles 160 are antennas that radiate an electromagnetic wave in response to flow of electric current, and in the context of EFEG, such current flows may correspond to brain activities, such as firing of neurons and conduction of neural signals across axons of the neurons. Therefore, detecting and recording the electromagnetic waves radiated by the brain 150 and performing source localization to determine electromagnetic waves radiated by each of current dipoles 160 can be used to study brain activity.

Multiple current dipoles 160 may correspond to different regions of the brain 150, and may radiate distinct electromagnetic waves that encode the activity of the respective regions of the brain 150. Due to the superposition principle that applies to electromagnetic waves, respective electromagnetic waves of the current dipoles 160 are linearly combined, or added together, at each location of the sensors 120 and manifest as local electric fields 170 that can be measured using the sensors 120. The local electric fields 170 are typically time-varying fields having multiple frequency components. In addition, in case of EFEG, the electric fields may substantially vary over a scale of centimeters. Therefore, measurement of electric fields that are local to the respective electric field sensor 120 is important. Furthermore, as the amplitude of the electric field decays with increasing distance between the source and the sensor, placing the electric field sensor 120 close to the source of the electric field can be beneficial for improved measurement sensitivity.

The measured local electric field 170 may contain contributions from multiple current dipoles 160, and for EFEG, it is desirable to decompose the contributions of each of the multiple current dipoles 160 to each of the measured local electric field 170 such that respective brain activities at regions of the brain modeled by each current dipoles 160 can be separated and reconstructed. Such decomposition may be performed, for example, using a Principal Component Analysis (PCA) technique. In general, such decomposition results in higher number of uncorrelated signals, or principal components, with higher number of measurements and higher signal-to-noise (SNR) ratio of the measurements. The EFEG system 100 using optically-probed electric field sensors 120 can provide both the high number of measurements and high SNR, which may in turn allow for greater number of current dipoles 160 in performing the decomposition, potentially increasing spatial resolution.

Figure 2:
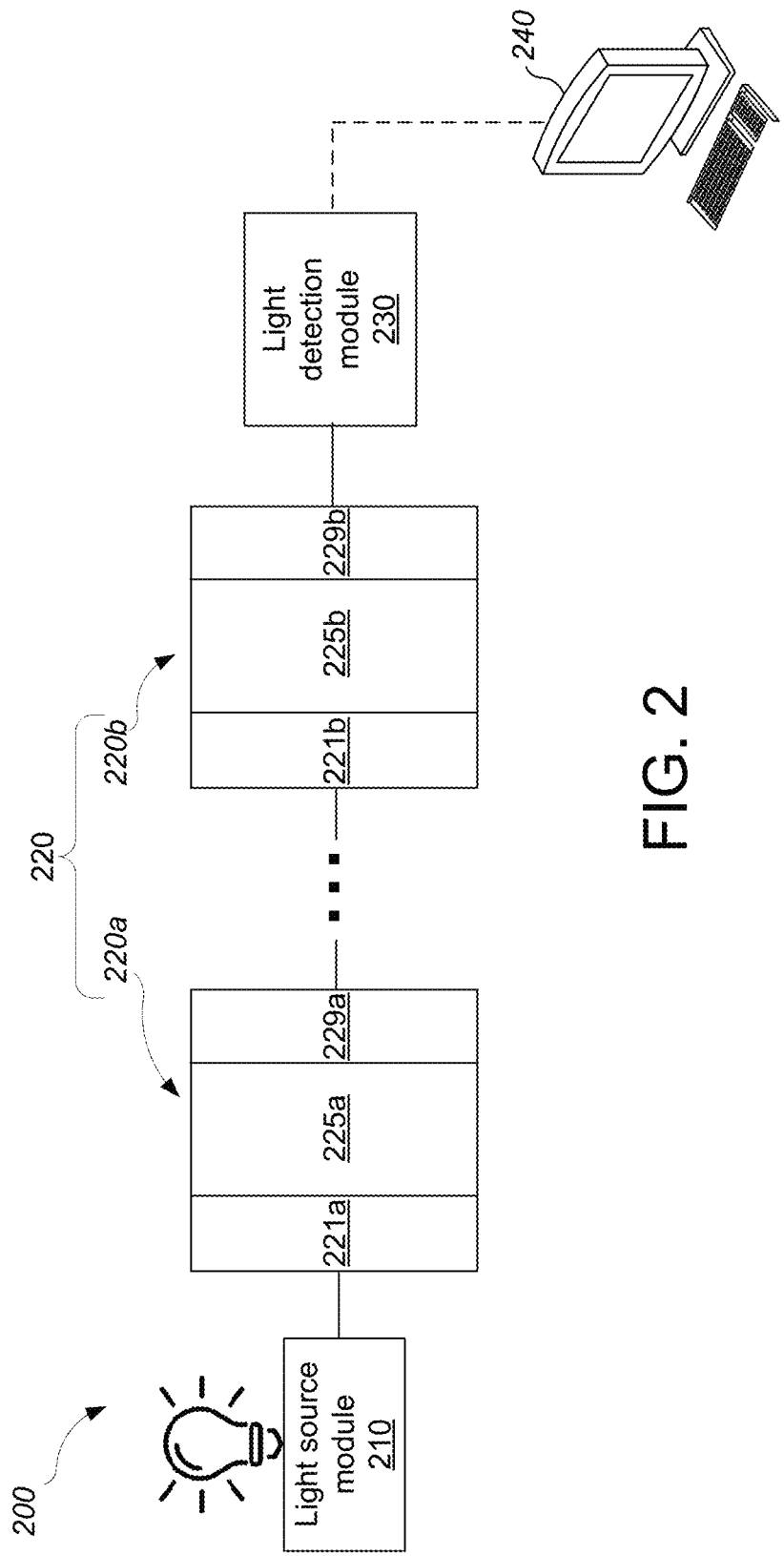
FIG. 2 shows an example of an optically probed multi-element electric field sensing system.

Referring to FIG. 2, an optically probed multi-element electric field sensing system 200 is shown. The system 200 includes a light source module 210, multiple electric field sensors 220a and 220b (collectively, electric field sensors 220), a light detection module 230, and a processing module 240. Each electric field sensor 220a or 220b includes a light input portion 221a or 221b (collectively, light input portion 221), an electro-optic (EO) material 225a or 225b (collectively, EO material 225), and a light output portion 229a or 229b (collectively, light output portion 229). The light source module 210, the electric field sensors 220, and the light detection module 230 are arranged such that a light generated by the light source module 210 travels along a common optical path through each of the electric field sensors 220 and is detected by the light detection module 230.

The common optical path can be provided in various ways. For example, the common optical path can be a path of light in free space. As another example, the common optical path can be an optical waveguide for confining the light along the waveguide. Examples of the optical waveguide include an optical fiber, a light guide, a dielectric waveguide, a channel waveguide, a rib waveguide, and a slot waveguide.

In general, the sensing system 200 can be configured in various ways based on a type and mode of operation of the electric field sensors 220. Examples of the mode of operation include wavelength division multiplexed (WDM) detection, spectrum detection, time of flight (TOF) detection, and frequency detection.

In general, the light source module 210 is configured to generate light having an intensity and wavelength(s) suitable for optically probing the electric field sensor 220. Various types of electric field sensors 220 may use different types of light (e.g., broadband, monochromatic, or a series of discrete wavelengths or wavelength bands).

In general, the electric field sensor 220 is configured to receive the light emitted from the light source module 210 through the light input portion 221. Within the electric field sensor 220, the electro-optic (EO) material is arranged in a path of at least some of the received light such that a property of the output light—which has interacted with the EO material—varies depending on the local electric field strength. In some implementations, an antenna can be provided in the sensor 220 to concentrate the local electric field at the sensor 220 to the EO material to enhance the sensitivity of the sensor 220. After passing through the EO material, the light encoding the local electric field strength at the electric field sensor 220 is output through the light output portion 229. Such an electric field sensor 220 can be implemented in various configurations.

Various types of materials can be used as the EO material 225. For example, materials exhibiting a linear electro-optic effect ("Pockels effect"), in which the refractive index of a medium is modified in proportion to the applied electric field strength, can be used as the EO material 225. Examples of such materials include lithium niobate ($LiNbO_3$), lithium tantalate ($LiTaO_3$), potassium di-deuterium phosphate (KD*P), β-barium borate (BBO), potassium titanium oxide phosphate (KTP), compound semiconductors such as gallium arsenide (GaAs) and indium phosphide (InP), transition metal dichalcogenides, and poled electro-optic polymers.

In general, the light detection module 230 is configured to detect light output by the electric field sensors 220, which encodes the local electric field strength information. The light detection module 230 generates electrical signals in response to the detected light and delivers these signals to the processing module 240. The signals delivered to the processing module 240 may be, for example, in form of analog voltages, analog currents, digitized values, or combination thereof. The communication path between the light detection module 230 and the processing module 240 may be wired or wireless communication path. Various types of electric field sensors 220 may use different types of light detection module 230 (e.g., WDM receiver, spectrometer, pulse repetition rate detector, free space detector).

In general, the processing module 240 is configured to analyze electrical signals from the light detection module 230 and determine, for each sensor, a corresponding value for a local electric field strength. Such analysis can be performed based on a calibration that maps a change in the property of the detected light to a value of local electric field strength. For example, the calibration can be based on design-time knowledge of the system, such as the electro-optic coefficient of the EO material 225 and the design and simulation of the electric field sensor 220. As another example, the calibration can be performed based on one or more applications of known electric field strengths at the sensors 220.

Optical signals generated by each electric field sensor 220 can be identified or separated in various ways. For example, in some implementations, a wavelength-division multiplexing (WDM) scheme can be used in which different wavelengths ("WDM lines") of monochromatic light are assigned to each of the sensors 220. In the WDM scheme, electric field sensor 220 may be configured to convert the local electric field strength to a change in transmission or reflection at the wavelength of the monochromatic light.

In the WDM scheme, the light source module 210 is configured to generate multiple lines of monochromatic light. Examples of a monochromatic light source include a laser diode, a solid-state laser, and a fiber laser. Multiple monochromatic light sources can be integrated and multiplexed to form a wavelength-division multiplexing (WDM) source. As another example, a frequency comb source can be used, which outputs multiple wavelengths of light spaced at a regular interval, forming a spectral "comb".

In the WDM scheme, the light detection module 230 is configured to demultiplex each WDM lines and separately detect each line. Examples of such a light detection module 230 include a WDM receiver.

In some implementations, spectrum detection is used to identify each electric field sensor 220 and perform electric field measurements. In the spectrum detection scheme, the light source module 210 is configured to generate a broadband light. The broadband light may be used to probe electric field sensor 220 of a type that converts the local electric field strength to a change in transmission or reflection spectra. Examples of a broadband light source include an amplified spontaneous emission (ASE) source, a supercontinuum source, a superluminescent diode, and a frequency comb.

In the spectrum detection scheme, the light detection module 230 is configured to spectrally resolve the received light. For example, the light detection module 230 can be a spectrometer that includes a dispersing element, such as a grating, and a sensor array arranged so that the location of the light on the array correlates to its wavelength.

In some implementations, a time of flight (TOF) detection scheme is used to identify each electric field sensor 220 and perform electric field measurements. In the TOF detection scheme, the light source module 210 is configured to generate pulses of light. Optical pulses may be used to probe the electric field sensor 220 of a type that converts the local electric field strength to a change in reflectivity. Examples of pulsed light source include a pulsed laser diode, a mode locked laser, or a frequency comb.

In the TOF detection scheme, the light detection module 230 is configured to determine the intensity of and temporally resolve multiple optical pulses arriving at different times. For example, the light detection module 230 can be operated in synchrony with the light source module 210. Such synchronization of the optical pulse generation and detection can enable TOF detection by enabling determination of a difference in time between a launch time when the optical pulse is emitted by the light source module and an arrival time of a reflected pulse that is detected by the light detection module.

In some implementations, a pulse repetition rate detection scheme is used to perform electric field measurements. In the pulse repetition rate detection scheme, the electric field sensor 220 can be configured to emit optical pulses at a pulse repetition rate that varies depending on the local electric field strength.

In the pulse repetition rate detection scheme, the light detection module 230 is configured to detect repetition rate of the pulses. For example, the light detection module 230 can be configured to count the number of pulses per unit time via a frequency counter, or determine the repetition rate by spectrum analysis via a spectrum analyzer.

Figure 3A:
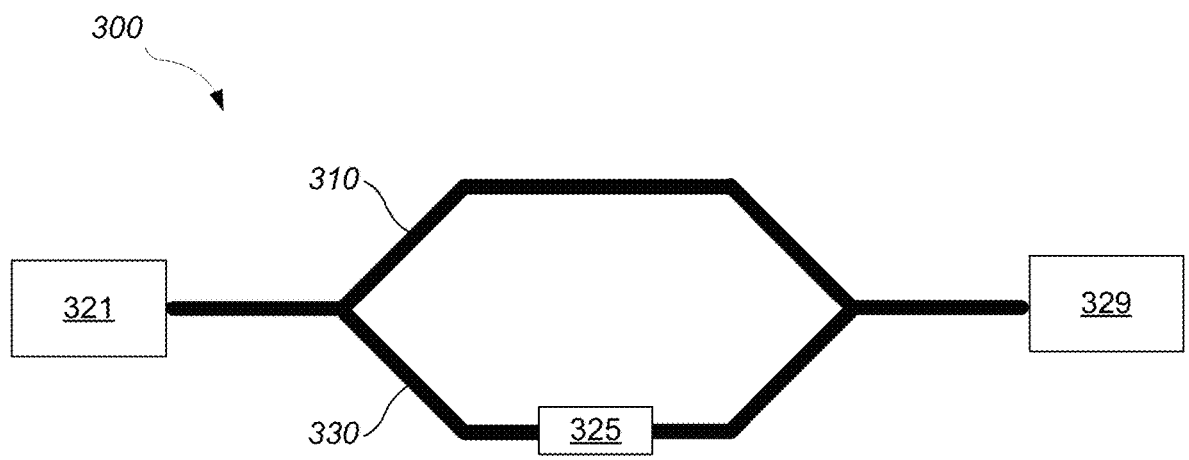
FIG. 3A shows an electric field sensor of the Mach-Zehnder type.

Turning now to specific sensor architectures, in some implementations, the electric field sensor 220 is implemented as a Mach-Zehnder interferometer. Referring to FIG. 3A, an electric field sensor 300 of the Mach-Zehnder type includes a light input portion 321, a first optical path 310, a second optical path 330, an EO material 325, and a light output portion 329. The electric field sensor 300, for example, can be used in the sensing system 200 implementing the WDM scheme. The light generated by the light source module is input to the sensor 300 through the light input portion 321, and travels along a common optical path before splitting into a first portion that travels along the first optical path 310 and a second portion that travels along the second optical path 330. While a Y-junction splitter is shown, the splitting of the light can be performed using various structures including a directional coupler and a beam splitter.

The first portion of light that travels along the first optical path 310 remains unaffected by the local electric field at the sensor 300, and serves as a reference light having a reference phase. The second portion of light travels through the EO material 325 placed along the second optical path 330, which modifies a property of the second portion of light. For example, for an EO material 325 whose refractive index changes in response to the local electric field strength, the phase of the second portion of light is modified relative to the reference phase of the first portion of light. Such change in the relative phase between the first and second portions of light is converted into a corresponding change in amplitude through optical interference when the two portions of light are combined before exiting through the light output portion 329. An example transfer function of the sensor 300 is shown in FIG. 3B.

Figure 3B:
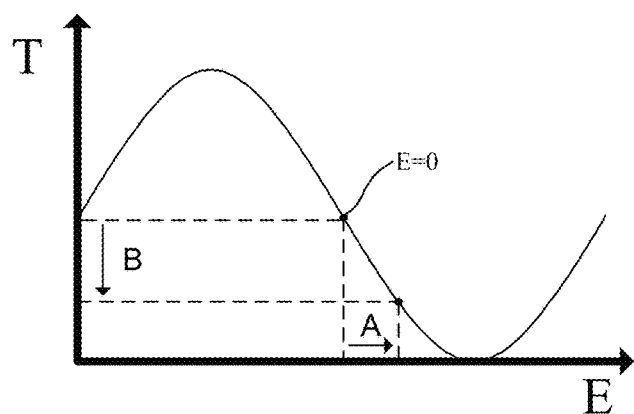
FIG. 3B shows an example transfer function of the electric field sensor shown in FIG. 3A.

FIG. 3B shows an example plot of a transmission T of the electric field sensor 300 on the y-axis as a function of local electric field strength E on the x-axis. This plot illustrates a sinusoidal dependence of the transmission versus the local electric field strength. In some operating conditions, the wavelength of the input light or an optical path length difference between the first and second optical paths can be configured such that the transmission of the electric field sensor is placed, or "biased", at a midpoint of the transfer function when no electric field is present. Such operating condition, or "bias point", leads to greatest change in transmission in response to the electric field strength E for a sinusoidal transfer function. When an electric field is applied to the sensor 300 as indicated by an arrow A, the transmission of the sensor 300 decreases accordingly as indicated by arrow B. When the electric field of an opposite sign is applied, the arrow A would point to the left, and the transmission of the sensor 300 would increase accordingly. Therefore, the output intensity of the light contains, or encodes, information regarding the local electric field strength at the sensor 300.

In general, increasing an interaction length of the light with the EO material 325 increases the sensitivity of the sensor 300. To this end, an optical delay line can be used to increase the interaction length of the light with the EO material. For example, an extended length of low-loss optical waveguide can be inserted in the second optical path 330 and arranged to interact with the EO material 325. To maintain a compact footprint of the sensor 300 and to maintain locality of the electric field measurement, the optical delay line can be coiled in a spiral shape. Due to the long physical length of the optical delay line, the change in the phase of the second portion of light in the second optical path 330 increases for a given electric field strength, increasing the sensitivity of the sensor 300.

Electric field sensors such as the Mach-Zehnder interferometer structure of FIG. 3A can be implemented using discrete free-space optical components, fiber-based components, or integrated optical components on a photonic integrated circuit (PIC) or a planar lightwave circuit (PLC).

In general, while the EO material 325 is shown to be placed along the second optical path 330, EO material can be placed in various locations of the sensor 300. For example, the EO material 325 can be placed on the first optical path 310. In some implementations, the sensor 300 can be formed on an EO material using, for example, waveguides defined on a Lithium Niobate substrate using methods such as proton exchange method. In such implementations, either one of the first or second optical paths can be electrostatically shielded such that the local electric field preferentially affects one path over the other path.

Sensitivity of the electric field sensor 220 can be improved by modification of the EO material or by addition of sensitivity-enhancing elements. For example, a second EO material having an electro-optic effect of opposite polarity relative to the EO material 325 can be placed on the first optical path 310. In such implementations, the sensitivity of the sensor 300 can be further increased. Example of a pair of EO materials having opposite EO effect is an electro-optic polymer that have been poled in opposite directions.

As another example, referring to FIG. 2, a saturable absorber can be cascaded at the light output portion 229 of the electric field sensor 220 to improve the sensitivity of the sensor. A saturable absorber is a nonlinear optical element that exhibits a nonlinear relationship between an intensity of an input light and intensity of a light output from the saturable absorber. For example, a saturable absorber attenuates ("absorbs") light when the input light intensity is below a certain threshold. As the input intensity increases beyond the threshold, the attenuation coefficient of the saturable absorber decrease (the absorber "saturates"), resulting in transmission of a higher percentage of input light relative to input light having intensity below the threshold.

Figure 3C:
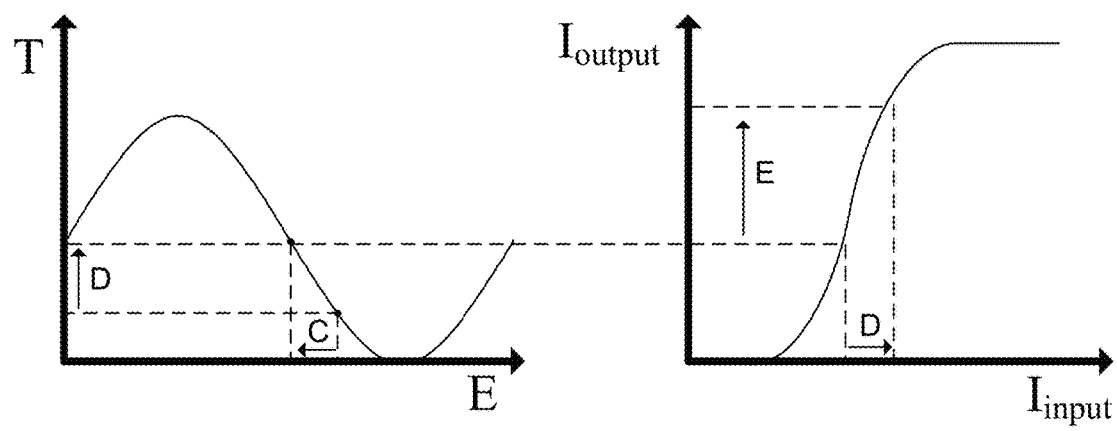
FIG. 3C shows an example of a transfer function of a saturable absorber.

Referring to FIG. 3C, an example of a transfer function of a saturable absorber is shown. On the left inset of FIG. 3C is an example transfer function similar to the transfer function of FIG. 3B to which a saturable absorber can be applied to improve the sensitivity of the sensor 220. In this example, an arrow C indicates a decrease in electric field E, and the change in electric field causes a corresponding increase in transmission T as indicated by an arrow D. On the right inset of FIG. 3C, the increase in transmission T directly corresponds to an increase in the input intensity $I_{input}$ of the saturable absorber as also indicated by the arrow D. The nonlinear transfer function of the saturable absorber translates the change in input intensity as indicated by arrow D to a larger change in the output intensity as indicated by an arrow E. Therefore, a magnitude of change in transmission caused by the local electric field strength is increased by inserting a saturable absorber after the light output portion 229.

As yet another example, a plasmonic waveguide can be used to guide light and enhance light-matter interaction with the EO material 225 to improve sensitivity of the sensor 220. A plasmonic waveguide can be formed using a dielectric material interfacing with a metal, providing a surface plasmon at the dielectric-metal interface, where electrons oscillate at the surface of the metal due to strong resonant interactions with the electric field of the guided light. The strong resonant enhancement can be utilized to enhance the EO effect of the EO material 225.

As still yet another example, an optical gain medium can be cascaded after the light output portion 229 of the electric field sensor 220 to improve the sensitivity of the sensor 220. An optical gain medium can amplify the power on an input light by a factor of its optical gain. The optical gain can be used to increase the effective slope of the transfer function of the electric field sensor 220, by amplifying the change in the intensity of the output light of the electric field sensor 220 induced by the local electric field strength. Examples of the optical gain medium include a semiconductor optical amplifier (SOA), rare-earth doped fiber, or a solid state gain medium.

Figure 3D:
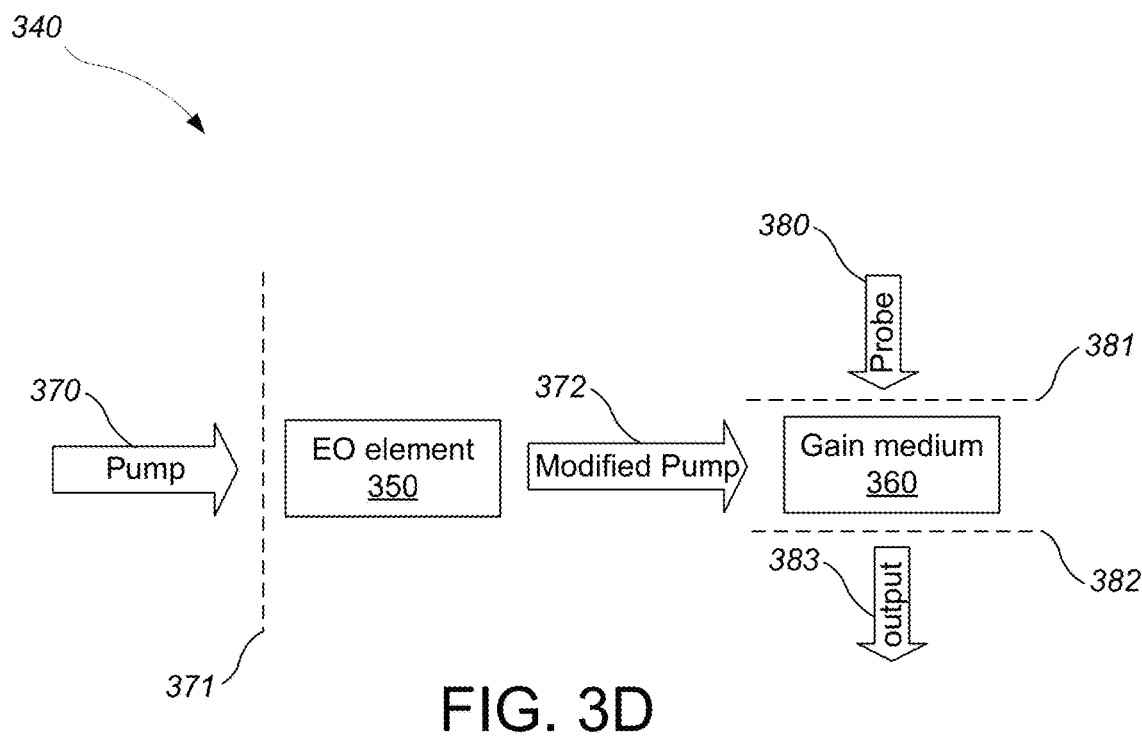
FIG. 3D shows an electric field sensor based on a pump-probe detection scheme.

In some implementations, the optical gain of the optical gain medium is probed using a second light, or a "probe light", to measure the local electric field strength. Referring to FIG. 3D, an electric field sensor 340 based on a pump-probe detection scheme is shown. The electric field sensor 340 includes an EO element 350 and an optical gain medium 360. A pump light 370 is received through a pump light input portion 371, and is input to the EO element 350, which outputs a modified pump light 372. The EO element 350 can be any optical element that exhibits a change in transmission in response to an application of an electric field. For example, the electric field sensor 300 can provide the EO element 350. The EO element 350 modifies the intensity of the pump light 370 based on the local electric field strength, encoding the local electric field strength information onto the intensity of the modified pump light 372.

The modified pump light 372 is then absorbed by, or "pumps", the optical gain medium 360 having an optical gain that varies depending on the intensity of the modified pump 372. A probe light 380 is received by a probe light input portion 381, and is input to the optical gain medium 360 to probe the optical gain of the optical gain medium 360. The probe light 380 is amplified by the optical gain of the optical gain medium 360, and is output by a probe light output portion 382 as an output probe light 383. The difference in intensity between the probe light 380 and the output probe light 383 is a direct measure of the optical gain of the optical gain medium 360, which in turn can be mapped to the intensity of the modified pump 372 which encodes the local electric field strength. Therefore, the difference in intensity between the probe light 380 and the output probe light 383 can be processed by the processing module 240 to determine the local electric field strength at the sensor 340.

While the direction of propagation of the modified pump light 372 and the probe light 380 is shown as being on a separate optical path, in general, optical paths of the pump light and the probe light can be arranged in various ways. For example, the pump and probe light can be co-propagating in the same direction along a common optical path through the gain medium 360. As another example, the pump and probe light can be counter-propagating in opposite directions along a common optical path through the gain medium 360.

An electric field sensor of the Mach-Zehnder type was described, but another type of the electric field sensor 220 can be implemented using an optical cavity incorporating an EO material. Referring to FIG. 4A, an electric field sensor 400 includes a first reflector 410, an EO material 425, and a second reflector 430. The electric field sensor 400, for example, can be used in the sensing system 200 implementing the WDM scheme or the broadband detection scheme. The first reflector 410 can provide the light input portion 221 and the second reflector 430 can provide the light output portion 229. The first reflector 410 and the second reflector 430 define an optical cavity, and the EO material 425 is arranged along a path of light within the optical cavity. An optical resonance of the optical cavity formed by the two reflectors leads to an increase in an interaction strength of the input light with the EO material 425, which can increase the sensitivity of the sensor 400 to the local electric field strength.

In some implementations, the first reflector 410 and the second reflector 430 are distributed Bragg reflectors (DBRs). A DBR includes an alternating stack of a first film 411 and a second film 412 having different refractive indices. By appropriately designing individual thicknesses of the alternating films, a reflector can be formed that reflects over a desired band ("stopband") of wavelengths and transmits wavelengths outside of the stopband. Referring to FIG. 4B, an example of a reflection spectrum of a DBR is shown. The reflectivity R of a DBR as a function of wavelength $\lambda$ is plotted. A first wavelength $\lambda_1$ and a second wavelength $\lambda_2$ marks the stopband of the DBR.

The first reflector 410 and the second reflector 430 of the DBR type can form a single DBR and incorporate the EO material 425. For example, the first or second films 411 or 412 can be formed from the EO material 425. In such implementations, the change in refractive index of the EO material 425 in response to a change in the local electric field strength can cause a change in effective optical thickness of the DBR, resulting in a change in the reflection spectrum of the sensor 400 (e.g., a shift along the wavelength axis). The change in the reflection spectrum can be detected using the light detection module 230 and processed by the processing module 240 to determine the local electric field strength.

Alternatively, or additionally, a defect layer can be provided between the first reflector 410 and the second reflector 430 that are of the DBR type. A defect layer is defined to be a layer that deviates from the alternating stacks of the first reflector 410 and the second reflector 430. For example, the thickness of the defect layer can be twice the thickness of adjacent layers. In this example, the EO material 425 provides the defect layer. The introduction of the defect layer creates a narrow band of transmission ("defect resonance") in the stopband of the reflectors 410 and 430. Incorporation of the EO material 425 within the defect layer causes the center wavelength of the defect resonance to shift in response to the local electric field strength, enabling electric field strength measurements.

Referring to FIG. 4C, an example of a reflection spectrum of the sensor 400 containing the defect layer as a function of wavelength is shown. Initially, in absence of a local electric field, the defect resonance of the defect layer is located at a first wavelength $\lambda 1$. Application of a local electric field E modifies the refractive index of the EO material 425 of the defect layer. The change in the refractive index of the EO material 425 results in a change in the effective optical path length of the defect layer, which shifts the spectral location of the defect resonance to a second wavelength $\lambda_2$. This change in the spectral location of the defect resonance in the reflected light can be detected using the light detection module 230 and processed by the processing module 240 to determine the local electric field strength.

Referring to FIG. 4D, an example of a transmission spectrum of the sensor 400 containing the defect layer as a function of wavelength is shown. Complementary to the reflection spectrum of FIG. 4C, the defect resonances manifest as transmission peaks in the transmission spectrum, and the locations of the defect resonances in the transmitted light can be measured and processed to determine the local electric field strength.

Figure 5A:
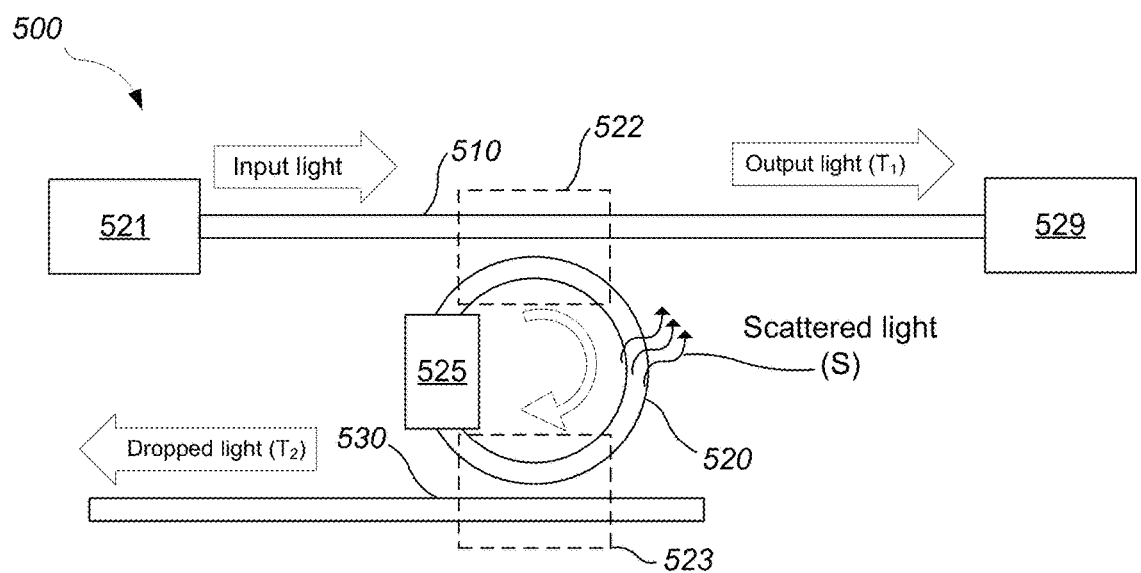
FIG. 5A shows an electric field sensor including a ring resonator optical cavity.

Yet another type of electric field sensor 220 can be implemented with a travelling wave optical cavity incorporating an EO material. Referring to FIG. 5A, an electric field sensor 500 includes a light input portion 521, a bus waveguide 510, a drop waveguide 530, a ring resonator 520, an EO material 525, and a light output portion 529. The electric field sensor 500, for example, can be used in sensing system 200 implementing the WDM scheme or the broadband detection scheme. The ring resonator 520 is an optical path that loops around itself to form a ring, and is typically formed on a photonic integrated circuit platform, such as silicon photonics or III-V PIC. The ring resonator 520 is optically coupled (e.g., via evanescent coupling) to the bus waveguide 510 and the drop waveguide 530.

The light generated by the light source module is input to the sensor 500 through the light input portion 521, and travels along the bus waveguide 510 until reaching the ring resonator 520. A portion of the input light couples to the ring resonator and propagates along the ring resonator 520 through the EO material 525, for example, in a clockwise direction in the example shown. After making a round trip around the ring resonator 520, the portion of light in the ring resonator 520 and the light present at a coupling region 522 of the ring resonator 520 proximal to the bus waveguide 510 form an optical interference, which results in a transmission spectrum with notch-shaped ring resonances.

The EO material 525 is arranged along the optical path of the ring resonator 520. For example, a thin film of Lithium Niobate can be placed on a silicon waveguide defining the ring resonator 520 such that a portion of the light guided within the ring resonator 520 interacts with the thin film of Lithium Niobate. A change in the refractive index of the EO material 525 changes an effective roundtrip optical path length of the ring resonator 520, which results in a modification of the resonance wavelength.

While the EO material 525 is shown to be placed along a portion of the ring resonator 520, the entire ring resonator 520 can be formed from the EO material 525. For example, the bus waveguide 510 and the drop waveguide 530 can be silicon waveguides on a first level, and the ring resonator 520 can be formed from an EO material on a second level that is sufficiently close to the first level to achieve optical coupling between the ring resonator 520 and the waveguides 510 and 530.

Figure 5B:
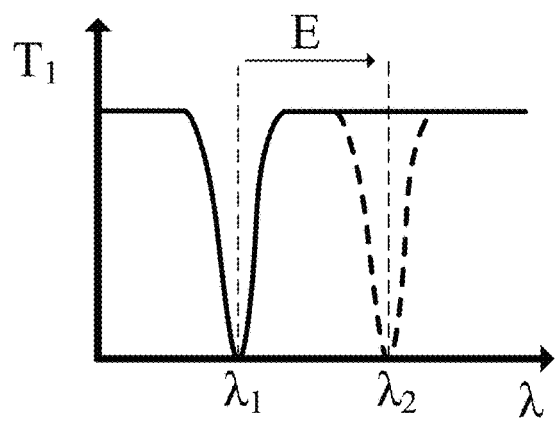
FIG. 5B shows an example of a transmission spectrum of the sensor shown in FIG. 5A.

Referring to FIG. 5B, an example of a transmission spectrum of the sensor 500 is shown. A transmission $T_1$ of the sensor 500 at the light output portion 529 as a function of wavelength $\lambda$ is plotted. In absence of a local electric field, the ring resonance in shape of a transmission notch is located at a first wavelength $\lambda_1$. Application of a local electric field E causes a shift in the spectral location of the ring resonance to a second wavelength $\lambda_2$. This change in the spectral location of the ring resonance in the transmitted light can be measured and processed to determine the local electric field strength.

Figure 5C:
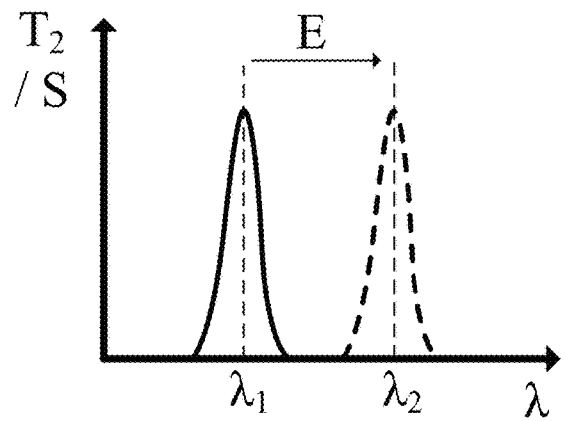
FIG. 5C shows an example of a spectrum of scattered or dropped light of the sensor shown in FIG. 5A.

Referring to FIG. 5C, an example of a spectrum of scattered or dropped light of the sensor 500 is shown. A spectrum of a scattered light S by the ring resonator 520, or dropped light at the drop waveguide 530 is plotted. Complementary to the transmission spectrum of FIG. 5B, the ring resonances manifest as peaks in the output spectrum of the drop waveguide 530 or the scattering spectrum of the ring resonator 520. The wavelengths of light not transmitted to the light output portion 529 by the ring resonator 520 can be coupled ("dropped") to the drop waveguide 530 at a coupling region 523 and/or dissipated (e.g., scattered) by the ring resonator 520. When the wavelength of the input light is aligned with the ring resonance wavelength, the optical interference at the coupling region 522 causes a buildup of intensity of the light at the resonance wavelength within the ring resonator 520. Such built-up light leads to an increase in scattered light S at the resonance wavelength. Such built-up light can also be coupled to the drop waveguide 530, resulting in transmission peaks that correspond to the ring resonances. In some implementations, a scattering element can be placed at the end of the drop waveguide 530 to facilitate scattering of light. The locations of the ring resonances in the dropped or scattered light can be measured and processed to determine the local electric field strength.

The scattered light S can be detected by the light detection module 520 configured to capture the scattered light via free space propagation. For example, a light detection module 520 configured to resolve a position of the source of the scattered light S can be used to determine the local electric field strength and map the determined field strength to the location of the electric field sensor 500. As another example, the light detection module 520 configured to spectrally resolve the received light can be used to identify the source of the scattered light and map the determined local electric field strength to the electric field sensor 500 based on WDM line-to-sensor mapping.

The dropped light of the drop waveguide 530 can be detected in various ways. For example, the dropped light can be routed to the light detection module 520 using an individual channel, using a dedicated optical fiber. In some cases, such use of an individual channel can reduce the complexity of the light detection module 520 or improve sensitivity of the electric field sensing system. As another example, the dropped light of the drop waveguide 530 can be locally detected at the electric field sensor 500 without external routing of the light to the light detection module 520. In case of a sensor 500 implemented on a photonic integrated circuit platform, photodiodes (e.g., germanium photodiode, InGaAs photodiode) can be formed at the end of the drop waveguide 530 to convert the dropped light into a photocurrent, which can be conveyed to the light detection module 230 to be converted into an intensity signal that can be processed by the processing module 240.

Figure 6A:
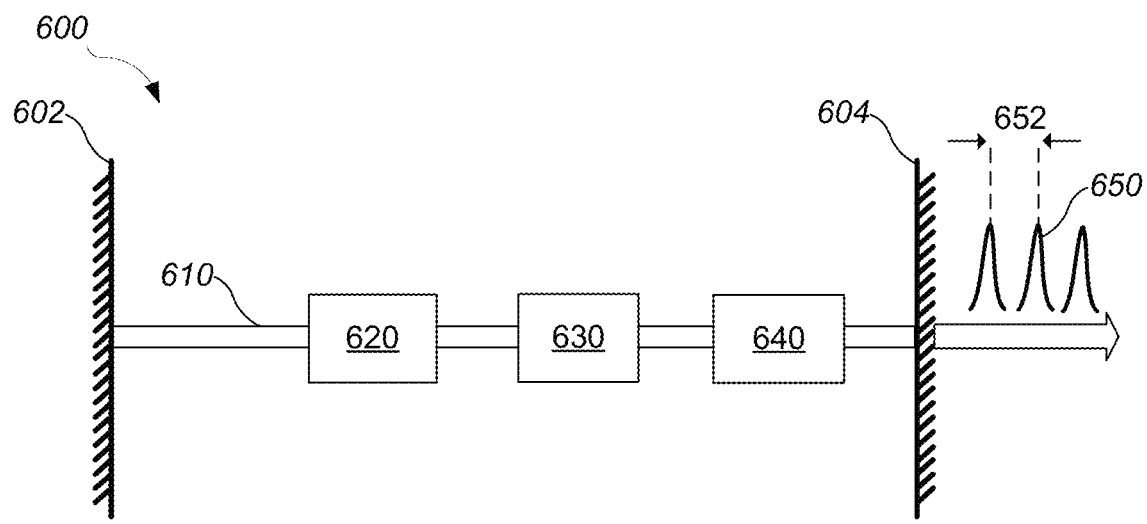
FIG. 6A shows an electric field sensor of the mode locked laser type.
Figure 6B:
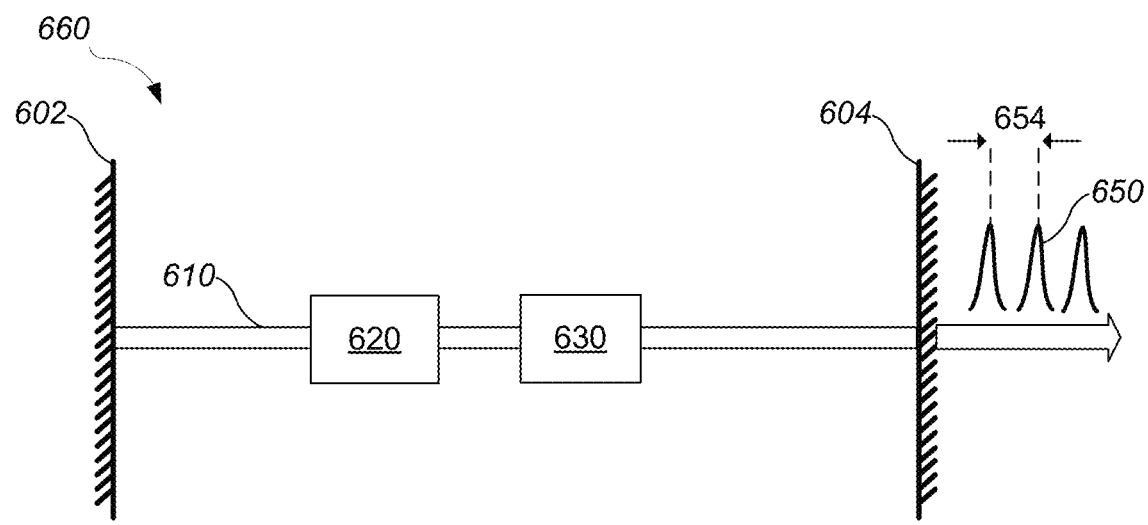
FIG. 6B shows a reference mode locked laser.

A different type of the electric field sensor 220, in which the sensor generates its own output light instead of modifying received probe light, can be implemented by modifying a mode locked laser (MLL). Referring to FIG. 6A, a mode-locked (ML) electro-optic (EO) sensor 600 includes a first reflector 602, a second reflector 604, an optical path 610, an optical gain medium 620, a mode-locking element 630, and an EO material 640. The first reflector 602 and the second reflector 604 define a laser cavity, and the optical gain medium 620, the mode-locking element 630, and the EO material 640 are arranged along the optical path 610 ("common path of light") within the laser cavity. In this example, the first reflector 602 is a high-reflectivity reflector, and the second reflector 604 is a partial-reflector configured to output laser light.

A mode locked laser is a class of laser that generates pulses of laser light through application of passive or active mode-locking techniques. The inclusion of the mode-locking element 630 in the sensor 600 is an example of an application of a passive mode-locking technique. The mode-locking element 630, for example, can be provided by the saturable absorber described in reference to FIG. 3C.

A passively mode-locked laser may operate based on the following example operating principle. As in a conventional continuous-wave (CW) laser, the properties of the optical gain medium 620 and the laser cavity defines a lasing wavelength. However, due to the saturable nature of the saturable absorber, bunching of the laser light in time is favored, as bunched light has a higher optical intensity which can saturate the absorption of the saturable absorber more than a CW light with lower intensities. After many round trips, a single pulse remains circulating in the laser cavity due to the positive feedback provided by the laser cavity, resulting in emission of laser pulses 650 at the second reflector 604 at every roundtrip of the single pulse. Accordingly, the laser pulses are emitted at a pulse repetition rate 652, which is proportional to an effective optical path length of the optical path 610. For example, the pulse repetition rate 652 is typically in the range of 100's of MHz to 100's of GHz.

The effective optical path length of the optical path 610 is proportional to the refractive indices of the materials through which the single pulse travels within the laser cavity. Therefore, an application of an electric field to the EO material 640 results in a corresponding change in the pulse repetition rate 650, which can be measured and processed to determine the local electric field strength.

An example method of determining the local electric field strength can include the following steps. First, the gain medium 620 of the sensor 600 is pumped to start generation of the laser pulses 650.

Second, the laser pulses 650 emitted by the sensor 600 are detected by the light detection module 230.

Third, the pulse repetition rate 652 of the laser pulses 650 is determined. For example, the light detection module 230 can be configured to count the number of pulses per unit time via a frequency counter, or determine the pulse repetition rate 652 by spectrum analysis via a spectrum analyzer.

Fourth, the local electric field strength at the sensor 600 is determined based on the pulse repetition rate 652. For example, a zero-field repetition rate of the laser pulses 650 corresponding to the pulse repetition rate 652 at zero local electric field strength at the sensor 600 is obtained during calibration. Then, a difference between the current pulse repetition rate 652 and the zero-field repetition rate can be converted to the local electric field strength using a conversion factor. For example, the calibration can be based on design-time knowledge of the system, such as the electro-optic coefficient of the EO material 640 and the design and simulation of the sensor 600. As another example, the calibration can be performed based on one or more applications of known electric field strengths at the sensors 600.

The optical gain medium 620 can be formed using a III-V semiconductor material, a single quantum well structure, II-VI semiconductor, quantum wire, quantum dot, or a multiple quantum wells structure.

The optical gain medium 620 can be optically pumped or electrically pumped. Electrical pumping does not require generation and routing of an optical pump light, which can be beneficial in simplifying the overall electric field sensing system.

In the case of optical pumping, an optical pump light can be generated using a pump light source located away from the region of measurement, and the pump light can be supplied to the sensor 600 by free space propagation or by an optical fiber. Such remote generation of the optical pump light and supplying of the pump light using an optical fiber can help reduce presence of conductors and electrical activities in the measurement region, which can reduce distortion of local electric field and EMI and improve the sensitivity of the electric field sensing system.

A reverse-biased semiconductor optical gain medium can function as a saturable absorber. As such, the mode locking element 630 can be provided by reverse-biasing a semiconductor optical gain medium. A separate section of optical gain medium can be provided and reversed biased to provide the mode locking element 630. Alternatively, a part of the optical gain medium 620 can be provided with a separate set of electrodes and reverse-biased to provide the mode locking element 630.

The mode locking element 630 can also be formed using graphene. For example, a layer of graphene can be placed on a surface of the optical waveguide to form a graphene-based saturable absorber waveguide suitable for passive mode locking. Graphene can be placed on the surface of the optical waveguide in various ways, including by direct chemical vapor deposition on the waveguide and by a graphene film transfer method.

Alternatively, the mode locking element 630 and the first reflector 602 or the second reflector 604 can be combined into a semiconductor saturable absorber mirror (SESAM) that provides the mode-locking element 630.

The ML-EO sensor 600 can be implemented in various platforms for optical circuits. In some implementations, the ML-EO sensor 600 is monolithically integrated on a common substrate. For example, the first and second reflectors 602 and 604, the gain medium 620, the mode locking element 630, and the EO material 640 can be integrated on a III-V semiconductor substrate (e.g., Indium Phosphide, Gallium Arsenide) of a photonic integrated circuit platform. An optical waveguide can be formed on the substrate to define the optical path 610 and guide light between the various components of the sensor 600. Using semiconductor planar processing techniques, each component of the sensor 600 can be formed on the III-V substrate through, for example, deposition, epitaxial growth, patterning, and etching of various materials. Another example of an integration platform is a hybrid III-V on silicon hybrid photonic integrated circuit platform.

Alternatively, the ML-EO sensor 600 can be implemented using fiber-based components. For example, the optical path 610 can be provided by an optical fiber, and the gain medium 620 can be provided by a rare-earth-doped fiber. Examples of rare-earth-doped fibers include erbium doped fiber, ytterbium-doped fiber, neodymium doped fiber, thulium doped fiber, and praseodymium doped fiber.

The sensitivity of the ML-EO sensor 600 can be improved by forming a second cavity around the EO material 640. The second optical cavity is configured to enhance a change in the effective optical path length of the light within the optical cavity in response to the local electric field strength by increasing an effective interaction length of the light with the EO material 640 by an optical resonance of the cavity. Examples of such second optical cavity include the DBR-based optical cavity of the electric field sensor 400 ("DBR defect cavity"), and the ring resonator-based optical cavity of sensor 500. Other examples include photonic crystal cavities and fiber gratings.

A method of determining the local electric field strength based on a comparison of the current pulse repetition rate of the ML-EO sensor 600 with its zero-field repetition rate was previously described. Alternatively, or additionally, field strength can be determined based on a comparison of the pulse repetition rate of the sensor 600 with that of a reference mode-locked laser. A reference mode-locked laser 660 can be similar to the sensor 600 but differs in that it lacks the EO material 640. By using the reference MLL 660, the measurement accuracy or the ease of calibration of a sensing system using the ML-EO sensor 600 may be improved. The reference MLL 660 has an optical cavity with a reference effective optical path length. The reference MLL 660 emits laser pulses 650 at a reference repetition rate 654 proportional to the reference effective optical path length. Due to the lack of EO material 640, the reference effective optical path length is not affected by a presence of local electric field and thus the reference repetition rate 654 is invariant to the local electric field strength. In such implementations, the processing module 240 can be configured to compare the repetition rate 652 against the reference repetition rate 654 and determine the local electric field strength based on the difference of the two repetition rates.

In some cases, it may be desirable to have a reference repetition rate 654 that is substantially equal to the repetition rate 652 of the ML-EO sensor 600 at zero local electric field strength. In such cases, forming the reference MLL to include the EO material 640 can improve matching of the reference repetition rate 654 to the zero-field repetition rate of the sensor 600. In some implementations, the reference MLL includes or is formed from the EO material 640 of the sensor 600. For example, both the reference MLL and the ML-EO sensor may be implemented using an optical waveguide formed on an InP substrate, which is an example of the EO material 640. In such implementations, the portion of the reference MLL formed from the EO material 640 can be electrostatically shielded such that the reference pulse rate 654 is unaffected by the local electric field strength In general, the repetition rate of a MLL can be affected by various environmental factors, such as ambient temperature. To mitigate such factors, in some implementations, the sensor 600 and the reference MLL 660 are placed in close proximity to one another. For example, the sensor 600 and the reference MLL 660 may be placed within 100 μm, 500 μm, 1 mm, 5 mm, or 10 mm of each other. By arranging the reference MLL 660 in close spatial proximity with the sensor 600, environmental factors may have equal effects on the respective repetition rates. Therefore, by comparing the repetition rate 652 against the reference repetition rate 654, any errors due to environmental effects can be canceled out, providing a more accurate electric field measurement.

The foregoing description of the electric field sensing system 200 was based on a series of electric field sensor 220 arranged along a common optical path. In general, the electric field sensors can be arranged in various ways.

Figure 7:
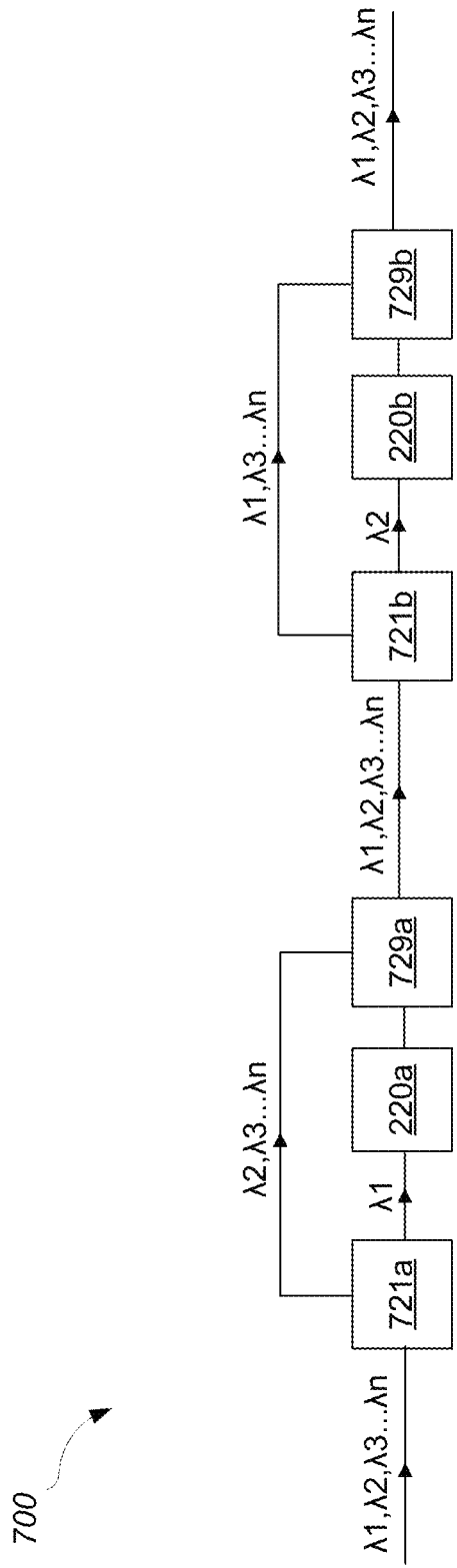
FIG. 7 shows an electric field sensor array implementing a wavelength bypass technique.

Referring to FIG. 7, an electric field sensor array 700 implementing a wavelength bypass technique is shown. The electric field sensor array 700 includes demultiplexers 721a and 721b, electric field sensors 220a and 220b, and multiplexers 729a and 729b. At the left of the array 700, a WDM light having multiple wavelengths $\lambda_1, \lambda_2, \lambda_3 \ldots \lambda_n$ is input to the sensor array 700. Each wavelength corresponds to a specific electric field sensor 220, $\lambda_1$ corresponding to sensor 220a and $\lambda_2$ corresponding to sensor 220b in this example.

The demultiplexer 721a is configured to demultiplex, or "drop", the first wavelength λ1. The first wavelength is routed to the electric field sensor 220a, and the remaining wavelengths bypasses the electric field sensor 220a through a separate optical path different from the optical path of the electric field sensor 220a.

The multiplexer 729a is configured to multiplex, or "add", the first wavelength $\lambda_1$ back to the bypassed wavelengths. At this point, the first wavelength $\lambda_1$ now encodes the local electric field strength at the sensor 220a. This wavelength bypass technique can enable use of electric field sensors that are not wavelength-specific. For example, the Mach-Zehnder-type sensor 200 generally affects all wavelengths that are input, which can corrupt other wavelengths that correspond to other sensors downstream to that sensor. By routing a specific wavelength that correspond to a specific sensor and bypassing the rest, such corruption can be mitigated. Use of the wavelength bypass technique can also improve density of WDM wavelengths which can enable formation of a larger sensor array, as multiplexers and demultiplexers can typically be designed to add or drop wavelengths that are spaced much more closely than, for example, the stop band of the DBR reflector of sensor 400.

Then, the WDM light is similarly demultiplexed, the demultiplexed second wavelength $\lambda_2$ routed to the electric field sensor 220b, and multiplexed again by the multiplexer 729b. While multiplexing and demultiplexing of two wavelengths are shown, this approach can be extended to a large number of wavelengths.

The multiplexers 721 and demultiplexers 729 can be provided by various components. In a photonic integrated circuit platform, a ring resonator can provide wavelength-by-wavelength multiplexing and demultiplexing. In a fiber platform, optical add-drop filters can provide individual wavelength multiplexing and demultiplexing.

Figure 8:
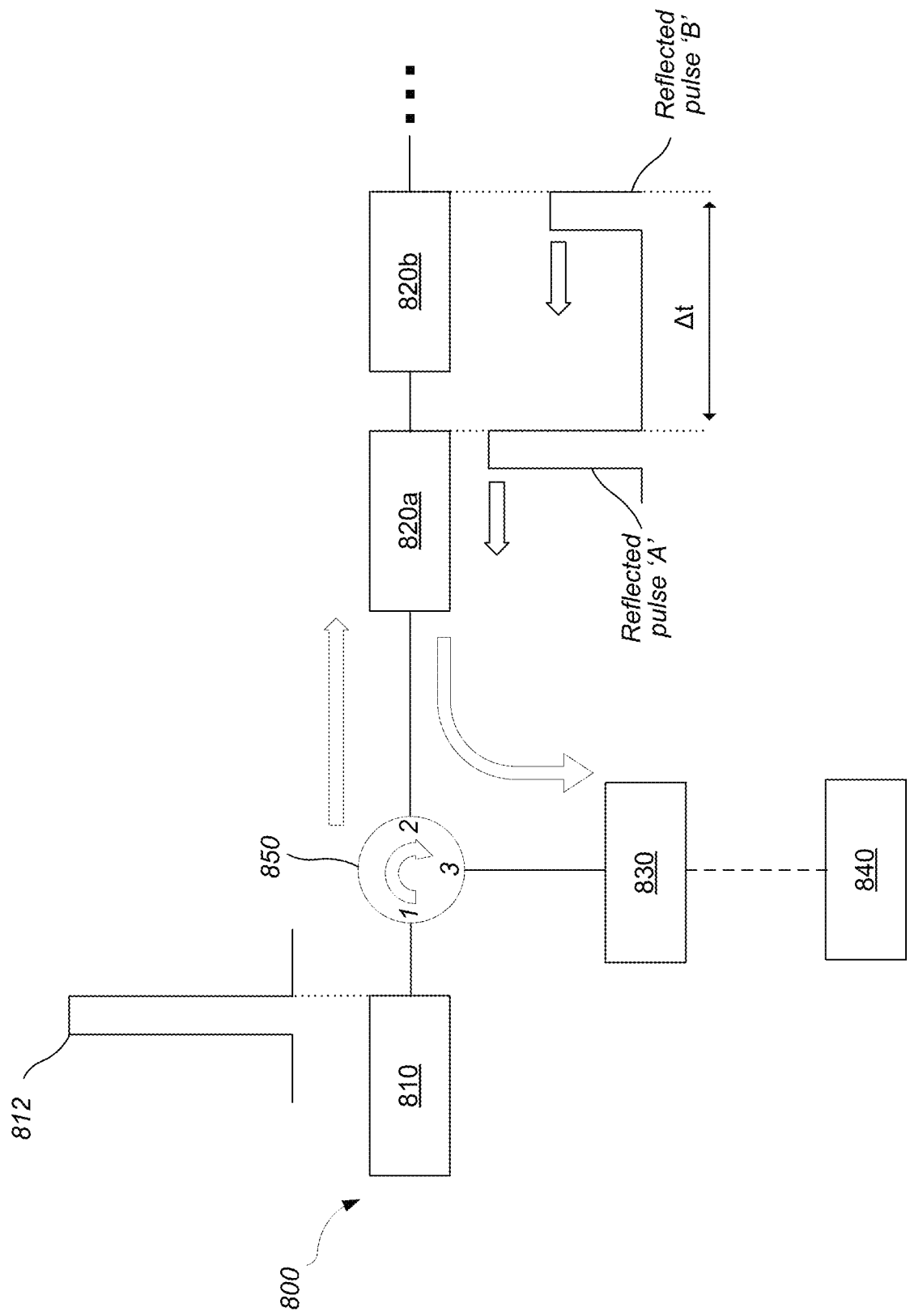
FIG. 8 shows an example of a reflection-based electric field sensing system.

While foregoing descriptions of the electric field sensing system 200 was based on transmission of light through a series of electric field sensor 220 arranged along a common optical path, a series of electric field sensors can be optically probed based on their reflections. Referring to FIG. 8, an example of a reflection-based electric field sensing system 800 includes a light source module 810, an optical circulator 850, reflective electric field sensors 820a and 820b, light detection module 830, and a processing module 840.

The optical circulator 850 is a non-reciprocal three-port device having first, second, and third ports that routes light, for example, input to the first port to the second port, and light input to the second port to the third port. This property of the circulator 850 enables launching of the input light at the first port and reception of reflected light at the third port. The light generated by the light source module 810 is input to a first port of the optical circulator 850, which then exits through the second port of the optical circulator 850.

The reflective electric field sensors 820a and 820b are configured to convert the local electric field strength to a change in reflectivity, reflecting a portion of the input light to encode the local electric field strength. An example of the reflective electric field sensor is the DBR-based electric field sensor 400. Other examples of reflective electric field sensors include ring resonator, fiber grating, and photonic crystal cavity including an EO material.

In the case of a fiber grating-based electric-field sensor, an EO material can be integrated into the cladding or core of the fiber that forms the fiber grating. For example, the fiber grating-based electric-field sensor can be implemented using a fiber-grating-based cavity. As another example, such sensor can be implemented using a fiber grating with a narrow stop band (e.g., long-period gratings with small effective index contrast).

When the input light reaches the first reflective electric field sensor 820a, a portion of the input light corresponding to a reflection band of the sensor 820a is reflected back towards the second port of the optical circulator 850. Similarly, the second sensor 820b reflects a corresponding portion of input light towards the second port of the circulator 850. The reflected light from the sensors 820a and 820b exits through the third port and is detected by the light detection module 830, which is then processed according to the detection scheme implemented by the system as previously described in relation to FIG. 2, such as WDM and spectrum-based schemes.

A time-of-flight (TOF) detection method can be used to resolve reflections encoding the electric field strength from the electric field sensors. To that end, in some implementations, the sensing system 800 can be configured to provide a TOF-based electric field sensing system.

The light source module 810 can be configured to generate an optical pulse 812 suitable for TOF measurements. In general, the duration of the pulse should be shorter than the roundtrip propagation time of the pulse from the reflecting locations. Examples of pulsed light source include a pulsed laser diode, a mode locked laser, and a frequency comb.

The reflective electric field sensor 820a is configured to convert the local electric field strength to a change in reflectivity, reflecting a portion of the input pulse and transmitting the remainder of the input pulse. When the input pulse 812 reaches the first reflective electric field sensor 820a, a reflected pulse A of a first amplitude is reflected back towards the second port of the circulator 850.

The reflected pulse A exits through the third port and is detected by the light detection module 830. The light detection module 830 is configured to determine the intensities of and temporally resolve multiple optical pulses arriving at different times. For example, the light detection module 830 can be operated in synchrony with the pulsed light source module 810. Such synchronization of the optical pulse generation and detection can enable TOF detection by enabling determination of a difference in time between a launch time when the optical pulse 812 is emitted by the light source module 810 and an arrival time of a reflected pulse at the light detection module. As another example, the processing module 840 can be configured to determine a relative timing between the launch time and the arrival time, for example, based on trigger signals or timestamps.

The measured TOF corresponds to the roundtrip optical path length along the optical path between the light source module 810, the reflective electric field sensor 820a, and the light detection module 830. Due to the serial arrangement of the sensors 820, the roundtrip optical path lengths to sensors downstream of sensor 820a increases monotonically. Therefore, determination of the TOF can be used to map the detected reflected pulse to a specific electric field sensor 820.

As each sensor 820 is configured to reflect a portion of the input pulse and transmit the remainder of the pulse, intensity of the pulse input to downstream sensors is modified by the preceding sensors. The processing module 840 can be configured to de-embed the influence of preceding sensors to extract an accurate value of the electric field strength. For example, the processing module 840 first determines the reflectivity of the first electric field sensor 820a, and based on the determination of the reflectivity of the first sensor 820a, determines the intensity of the transmitted pulse that is input to the second sensor 820b. The processing module 840 then determines the reflectivity of the second sensor 820b based on the detected reflection corresponding to the second sensor 820b and the calculated, or "de-embedded", input pulse intensity to the second sensor 820b. The detected reflection of the second sensor 820b is also de-embedded based on the reflectivity of the first sensor 820a, as a portion of the reflected pulse B is reflected by the first sensor 820a. In general, this de-embedding can be extended to multiple sensors 820. Additionally, any spurious reflections, such as reflection of the reflected pulse B by the first sensor 820a, which in turn is reflected again by the sensor 820b and detected by the detection module 830, can be identified and discarded or otherwise appropriately processed based on known path lengths of the system 800.

Figure 9A:
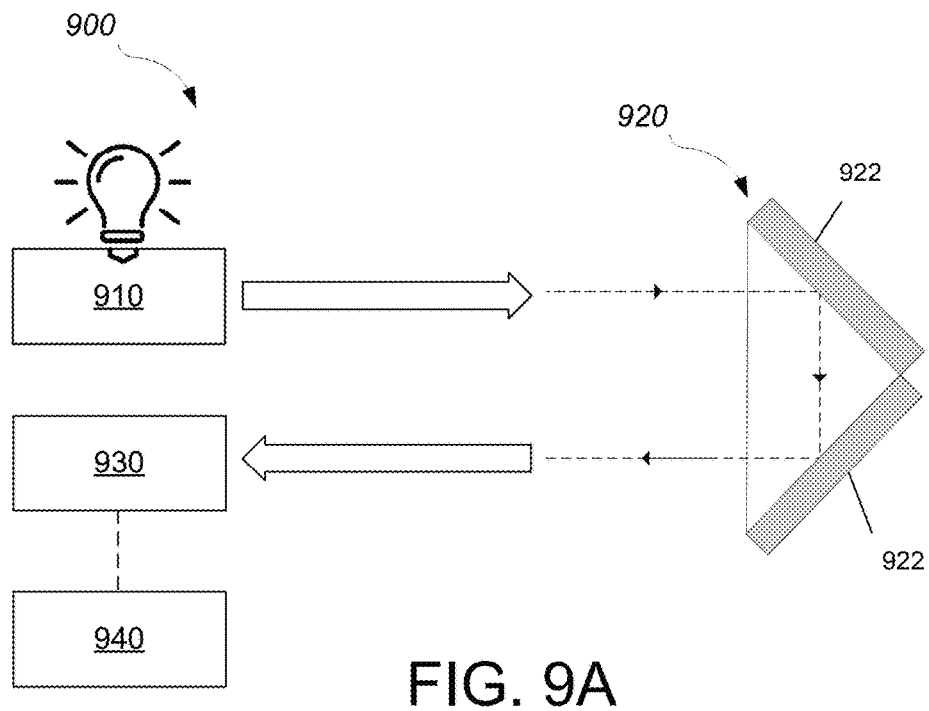
FIG. 9A shows an example of a retroreflection-based electric field sensing system.

The reflection-based electric field sensing system 800 described above is based on reflective sensors 820 connected in series along a common optical path. However, a reflection-based electric field sensing system based on free-space propagation of light can be implemented. Referring to FIG. 9A, an electric field sensing system 900 based on retroreflecting electric field sensors is shown. The retroreflection-based electric field sensing system 900 includes a light source module 910, retroreflecting electric field sensors 920, light detection module 930, and a processing module 940.

Retroreflectors, e.g., cube corner reflectors, are optical devices which reflect light back along the path from which it came. The retroreflecting electric field sensor 920 can be implemented with reflecting elements 922 that are sensitive to the local electric field by incorporation of an EO material. For example, in some implementations, the reflecting element 922 is formed from a Distributed Bragg reflector (DBR) that includes a defect formed from an EO material, similar to the DBR defect cavity of sensor 400. Such DBR-based reflecting element 922 can exhibit broadband reflection with a narrow passband that is sensitive to the local electric field, enabling electric field strength measurements based on retroreflected light.

The light source module 910 can be configured to emit broadband light over a region that includes the retroreflecting sensor 920, and the light detection module 930 can be configured to spatially and spectrally resolve the retroreflected light to allow determination of the electric field strength and map the determined field strengths to the various locations of the retroreflecting sensors 920.

Figure 9B:
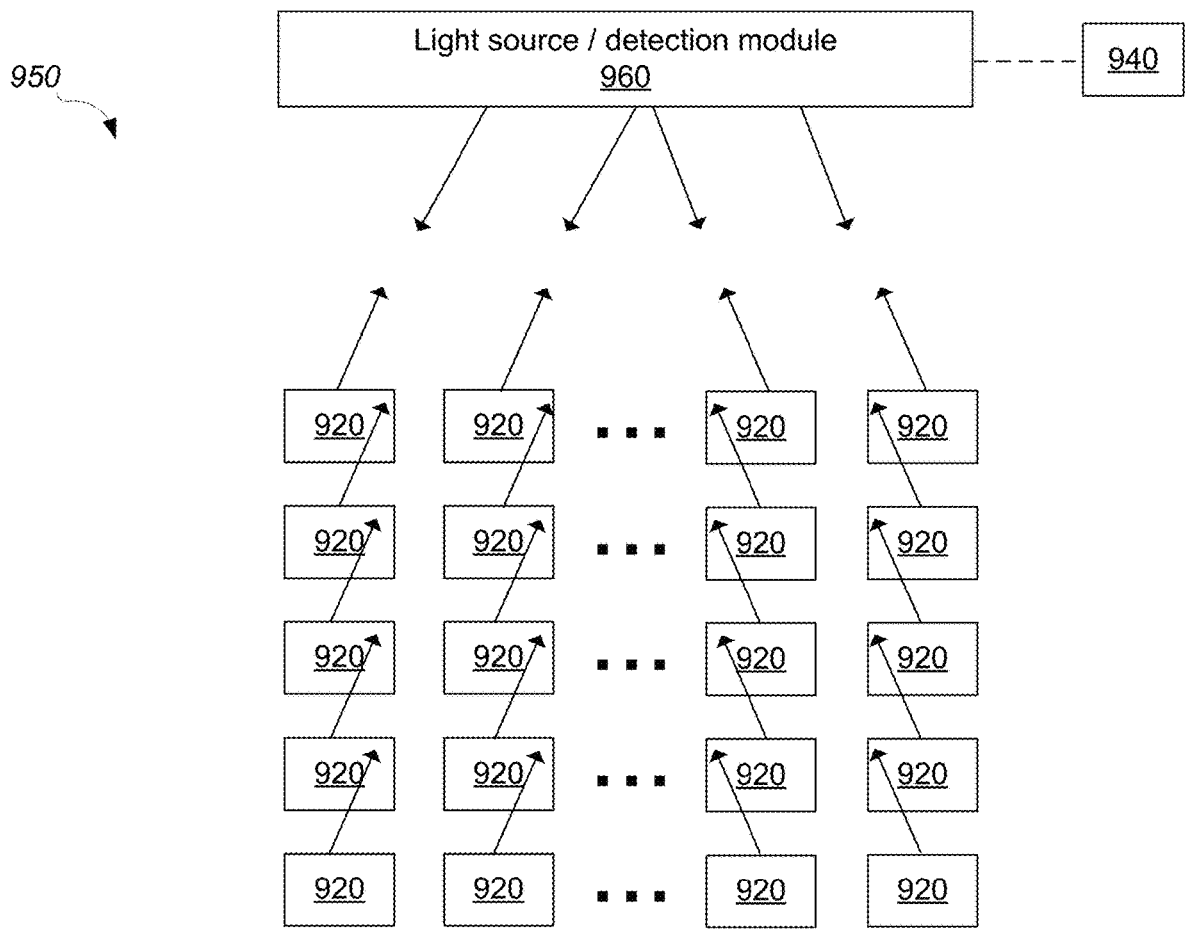
FIG. 9B shows an example of an electric field sensing system based on a two-dimensional array of retroreflecting electric field sensors.

Electric field sensing systems based on retroreflecting electric field sensors can be beneficial for performing multi-point electric field strength measurements of a non-stationary object. Referring to FIG. 9B, an example of an electric field sensing system 950 based on a two-dimensional array of retroreflecting electric field sensors is shown. The sensing system 950 includes an array of the retroreflecting sensors 920, a combined light source and detection module 960, and the processing module 940.

The combined light source and detection module 960 integrates the light source module 910 and light detection module 930 into one physical module. Such integration is beneficial for use with retroreflecting sensors 920, as it enables efficient detection of the retroreflected light which is typically reflected to a point close to the source of the light.

In context of the electric field encephalography (EFEG) system 100, an array of the retroreflecting sensors 920 of the sensing system 950 can be fixed on a head of a subject. Such placement of the sensors enables relative locations of the sensors with respect to regions of the brain to be maintained while the subject is moving. Therefore, measured electric field strengths can be more accurately mapped to various regions of the brain to improve quality of measurement for EFEG applications.

While a retroreflecting sensor 920 having electric field-sensitive reflecting element 922 is shown, other configurations for the retroreflecting sensor 920 are possible. For example, in some implementations, the reflecting element 922 is a non-electric field-sensitive reflector, and an electric field sensor described in the present disclosure can be arrange along a path of light within the retroreflecting sensor 920 such that the reflected light of the retroreflecting sensor 920 encodes the local electric field strength.

As another example, the retroreflecting sensors 920 can be configured to locally generate light for encoding the local electric field strength. For example, the light source and detection module 960 can be configured to provide a pump light. The pump light can be received by the sensors 920 and used to excite a local light emitter such as a broadband luminescent material or an optical gain medium. The resulting light generated by the local emitters can encode the local electric field strength and be transmitted back towards the module 960 by retroreflection. For example, an optical gain medium can be integrated into the DBR-type reflecting element 922 of the retroreflecting sensor 920, which is pumped by the received pump light. The resonant property of the DBR-type reflecting element 922 can cause emission of an output light that peaks at the defect resonance. Such emission is reflected back towards the module 960, which can be detected then processed by the processing module 940 to identify the location of the sensor and determine the local electric field strength.

Figure 10:
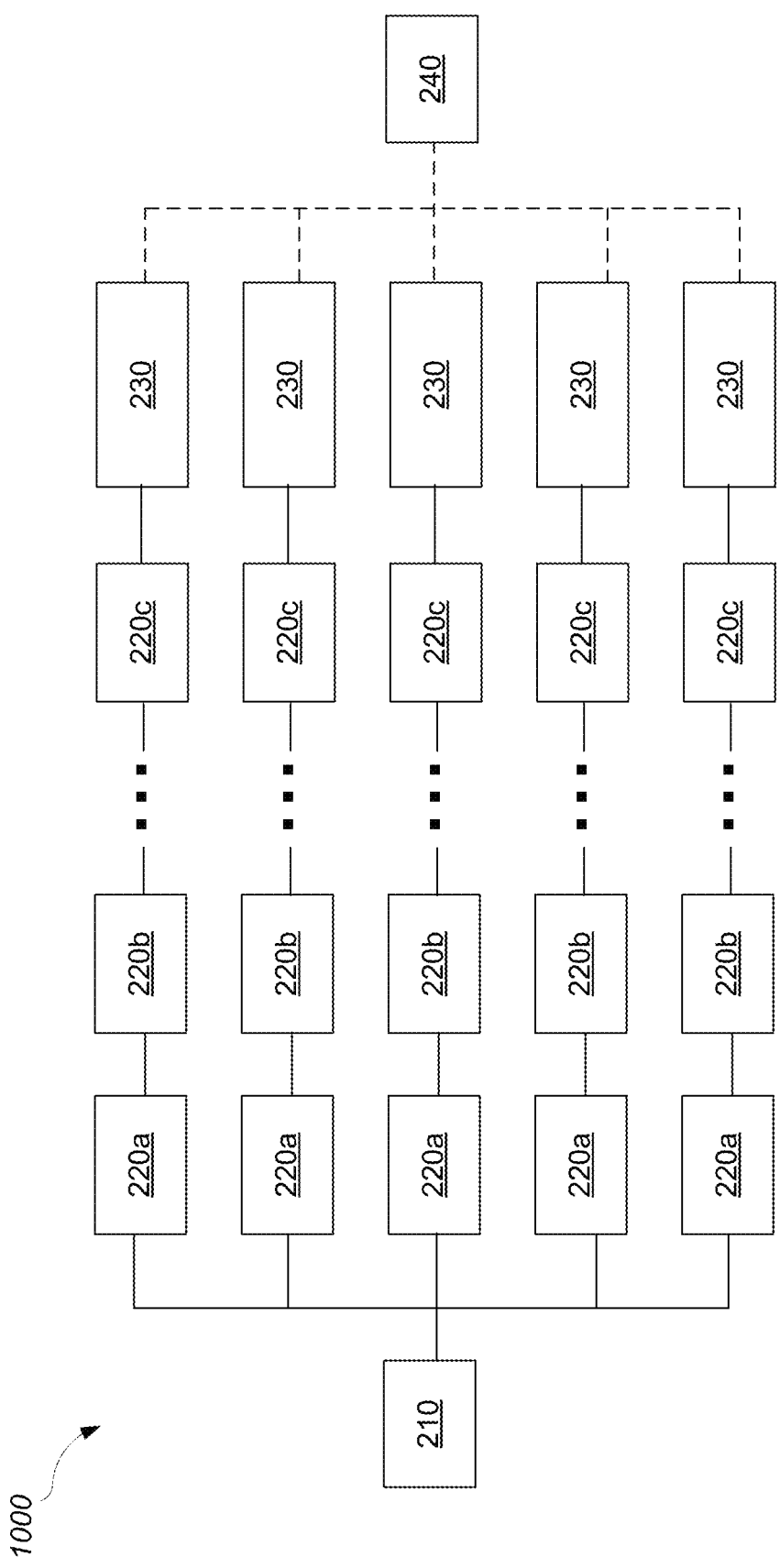
FIG. 10 shows an example of an arrayed electric field sensing system.

While an electric field sensing system 950 based on a two-dimensional array of retroreflecting electric field sensors is described, in general, other types of electric field sensors can be used to form a two-dimensional arrayed sensing systems. Referring to FIG. 10, an arrayed electric field sensing system 1000 is shown. The sensing system 1000 includes the light source module 210, multiple electric field sensors 220a to 220c, light detection modules 230, and a processing module 240.

The light source module 210 provides the input light to each group of electric field sensors 220a to 220c. For example, each row of electric field sensors 220a to 220c can constitute a group. Each row of electric field sensors is arranged along a common optical path, and each row functions as previously described in relation to FIG. 2. The light detection modules 230 each detect the output light of respective rows of the electric field sensors 220a to 220c, and the processing module 240 processes the output of the multiple light detection modules 230 to determine a two-dimensional map of electric field strengths.

In some implementations, the common optical paths of the groups of sensors are arranged parallel to each other to form a grid, or a rectangular array, of sensors. In some implementations, the common optical paths are spatially arranged to intersect each other at a perpendicular angle, such that the electric field sensors and the common optical paths are arranged to form a grid.

Figure 11:
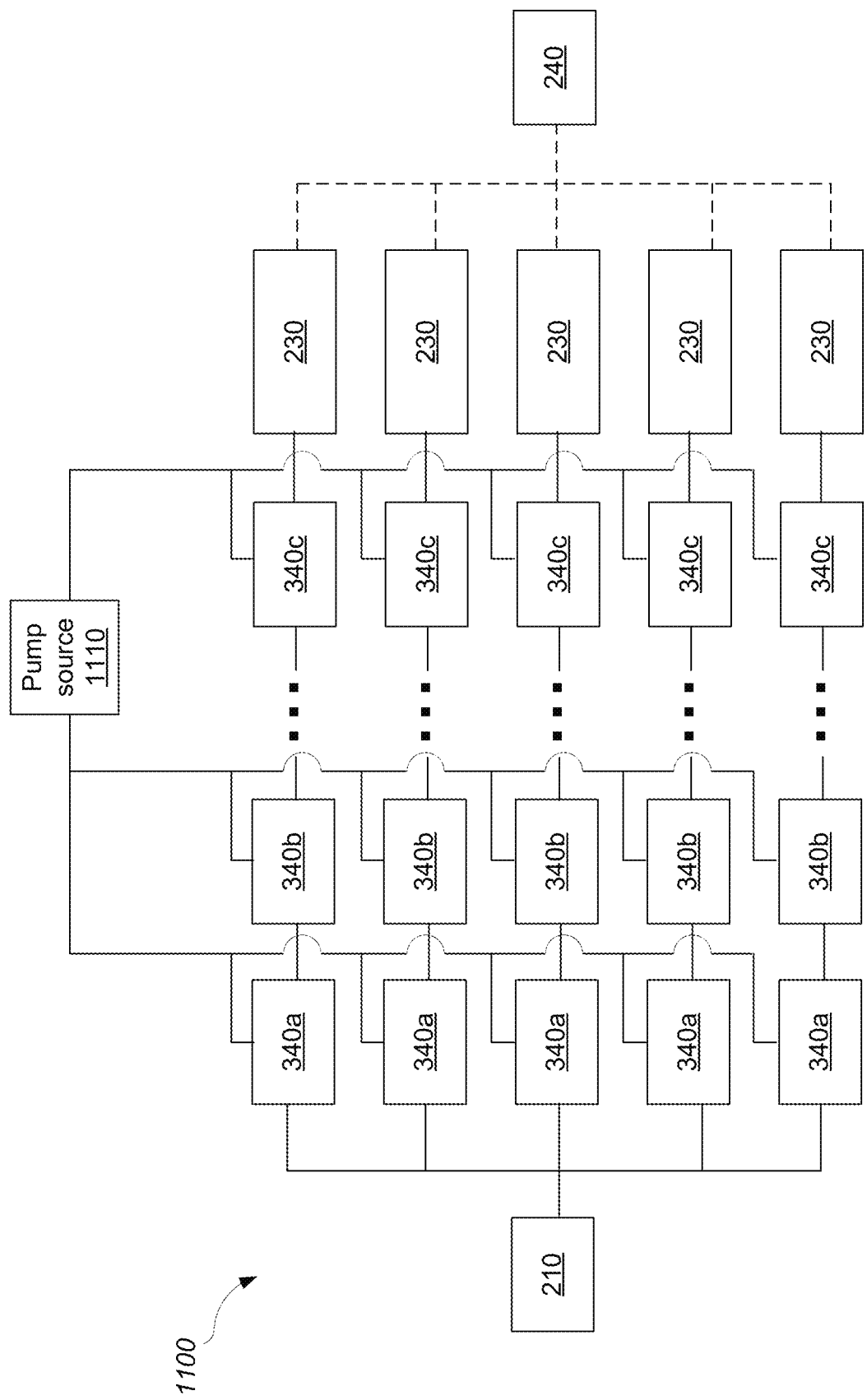
FIG. 11 shows an example of an arrayed electric field sensing system based on pump-probe electric field sensors.

Referring to FIG. 11, an arrayed electric field sensing system 1100 based on pump-probe electric field sensors 340 is shown. The sensing system 1100 includes the light source module 210, multiple pump-probe electric field sensors 340a to 340c, a pump source module 1110, light detection modules 230, and a processing module 240.

The pump probe sensors 340 are similarly arranged to the sensors 220 of the arrayed sensing system 1000. The pump light generated by the pump source module 1100 is supplied to each sensors 340 through respective pump light input portions 371. The probe light generated by the light source module 210 is supplied to each sensors 340 through respective probe light input portions 381 of the first sensors 340a. As sensors 340 are not a wavelength-specific sensors, the light source module 210 is configured to emit WDM light, and the wavelength-bypass scheme described in relation to FIG. 7 is used so that each of the WDM lines along a row of sensors encodes electric field information of a single sensor 340. In some implementations, the common optical paths of the groups of sensors 340 are arranged parallel to each other to form a grid, or a rectangular array, of sensors.

Some aspects of the optically probed multi-element electric field sensing system described here can be implemented in digital electronic circuitry, or in computer software, firmware, or hardware, including the structures disclosed in this specification and their structural equivalents, or in combinations of one or more of them. For example, in some implementations, the computer controller 190 can be implemented using digital electronic circuitry, or in computer software, firmware, or hardware, or in combinations of one or more of them.

The term "processing module" encompasses all kinds of apparatus, devices, and machines for processing data and/or control signal generation, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes described above can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computing system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 12:
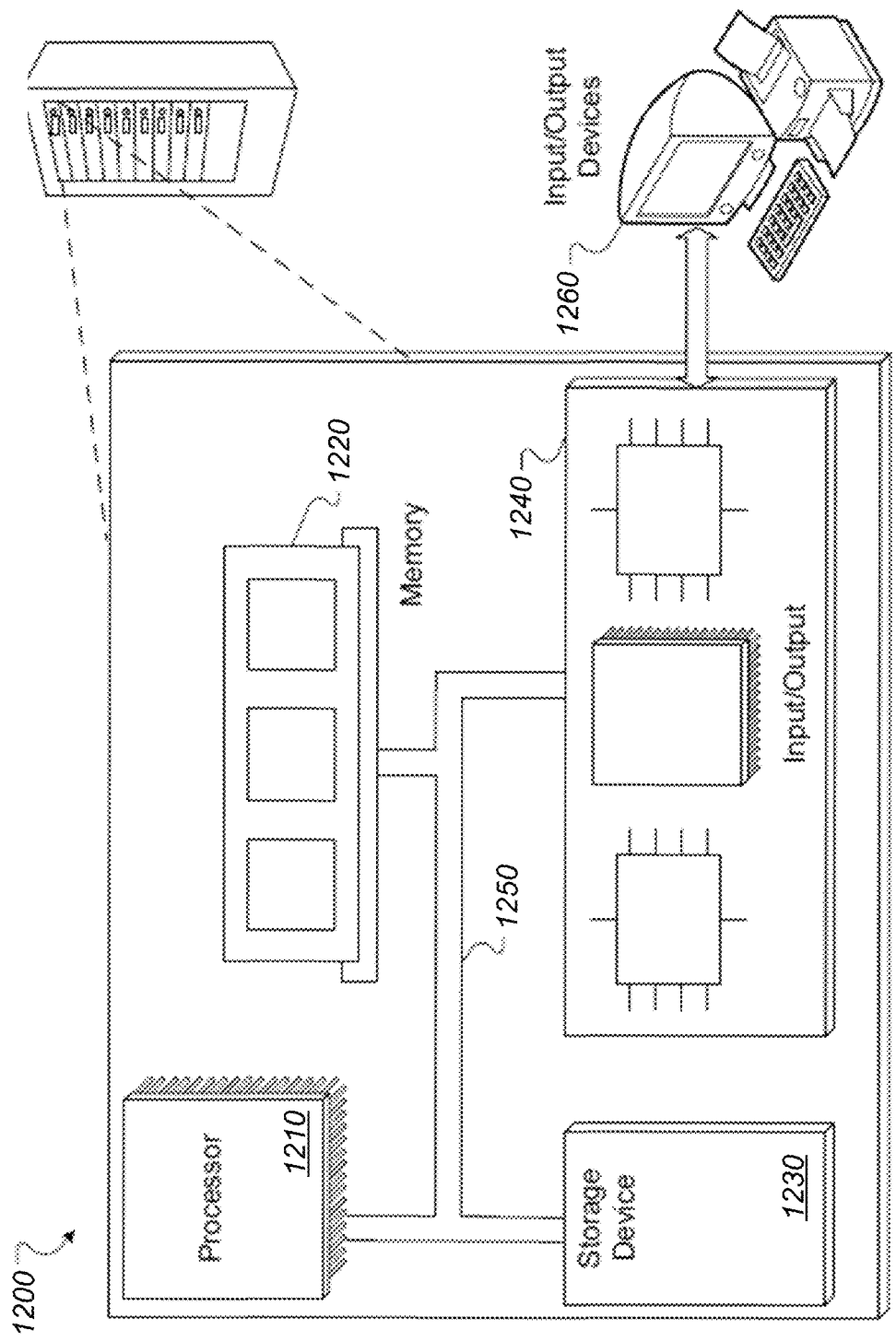
FIG. 12 shows an example computing system.

FIG. 12 shows an example computing system 1200 that includes a processor 1210, a memory 1220, a storage device 1230 and an input/output device 1240. Each of the components 1210, 1220, 1230 and 1240 can be interconnected, for example, by a system bus 1250. The processor 1210 is capable of processing instructions for execution within the system 1200. In some implementations, the processor 1210 is a single-threaded processor, a multi-threaded processor, or another type of processor. The processor 1210 is capable of processing instructions stored in the memory 1220 or on the storage device 1230. The memory 1220 and the storage device 1230 can store information within the system 1200.

The input/output device 1240 provides input/output operations for the system 1200. In some implementations, the input/output device 1240 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1260. In some implementations, mobile computing devices, mobile communication devices, and other devices can be used.

A number of embodiments have been described. Nevertheless, it will be understood that various modifications may be made without departing from the spirit and scope of the invention. Accordingly, other embodiments are within the scope of the claims.

What is claimed is:

1. A system comprising:
a light source module configured to emit light;
a plurality of electric field sensors, each sensor comprising a light input portion configured to receive light emitted from the light source module and a light output portion configured to output light in response to the received light, each sensor comprising an electro-optic material arranged in a path of at least some of the received light, an optical property of the electro-optic material being variable depending on a local electric field strength at the sensor, and the electro-optic material being arranged in the sensor such that a property of the output light varies depending on the local electric field strength;
a light detection module arranged to receive the output light from the sensors; and
a processing module in communication with the light detection module, the processing module being programmed to determine a corresponding value for the electric field strength local to each of the sensors based on the detected output light from each respective sensor, wherein each of the plurality of electric field sensors comprises a plasmonic waveguide.

2. The system of claim 1, wherein the light emitted by the light source module comprises a plurality of wavelengths, the plurality of electric field sensors being responsive to one or more corresponding wavelengths of the plurality of wavelengths,
the light detection module being configured to separately detect light at each of the corresponding one or more of the plurality of wavelengths, and
the processing module being programmed to determine corresponding local electric field strength at each of the sensors based on the detected wavelengths of light corresponding to each sensor.

3. The system of claim 2, wherein the plurality of electric field sensors are arranged at different locations along a common optical path of the light from the light source module.

4. The system of claim 3, wherein the common optical path comprises an optical waveguide.

5. The system of claim 3, wherein each of the plurality of electric field sensors comprises a multiplexer and a demultiplexer.

6. The system of claim 2, further comprising an optical circulator optically coupled to the light source module, the plurality of electric field sensors, and the light detection module.

7. The system of claim 6, wherein the light source module emits optical pulses during operation and the processing module is programmed to correlate each of a plurality of detected optical pulses to a corresponding electric field sensor based on a respective arrival time of the detected optical pulse.

8. The system of claim 1, wherein the light emitted by the light source module comprises a plurality of wavelengths and the plurality of electric field sensors each have a respective resonant wavelength which vary depending on the electric field strength local to the respective electric field sensor.

9. The system of claim 1, wherein the electro-optic material is selected from the group consisting of: lithium niobate, lithium tantalate, potassium di-deuterium phosphate, (β-barium borate, potassium titanium oxide phosphate, gallium arsenide, indium phosphide, transition metal dichalcogenides, and poled electro-optic polymers.

10. A system comprising:
a light source module configured to emit light;
a plurality of electric field sensors, each sensor comprising a light input portion configured to receive light emitted from the light source module and a light output portion configured to output light in response to the received light, each sensor comprising an electro-optic material arranged in a path of at least some of the received light, an optical property of the electro-optic material being variable depending on a local electric field strength at the sensor, and the electro-optic material being arranged in the sensor such that a property of the output light varies depending on the local electric field strength;
a light detection module arranged to receive the output light from the sensors; and
a processing module in communication with the light detection module, the processing module being programmed to determine a corresponding value for the electric field strength local to each of the sensors based on the detected output light from each respective sensor,
wherein the light emitted by the light source module comprises a plurality of wavelengths,
wherein the plurality of electric field sensors comprises a plurality of retroreflectors configured to retroreflect the light received by the plurality of electric field sensors, the plurality of electric field sensors each having a respective resonant wavelength which vary depending on the electric field strength local to the respective electric field sensor,
wherein the retroreflector is a cube corner retroreflector, and
wherein the electro-optic material is integrated with the cube corner to form a reflective surface of the cube corner.

11. The system of claim 10, wherein the light emitted by the light source module comprises a plurality of wavelengths, the plurality of electric field sensors being responsive to one or more corresponding wavelengths of the plurality of wavelengths,
the light detection module being configured to separately detect light at each of the corresponding one or more of the plurality of wavelengths, and
the processing module being programmed to determine corresponding local electric field strength at each of the sensors based on the detected wavelengths of light corresponding to each sensor.

12. The system of claim 11, wherein the plurality of electric field sensors are arranged at different locations along a common optical path of the light from the light source module, and
wherein the common optical path comprises an optical waveguide.

13. The system of claim 12, wherein each of the plurality of electric field sensors comprises a multiplexer and a demultiplexer.

14. The system of claim 11, further comprising an optical circulator optically coupled to the light source module, the plurality of electric field sensors, and the light detection module.

15. The system of claim 14, wherein the light source module emits optical pulses during operation and the processing module is programmed to correlate each of a plurality of detected optical pulses to a corresponding electric field sensor based on a respective arrival time of the detected optical pulse.

16. The system of claim 10, wherein the light emitted by the light source module comprises a plurality of wavelengths and the plurality of electric field sensors each have a respective resonant wavelength which vary depending on the electric field strength local to the respective electric field sensor.

17. The system of claim 10, wherein the electro-optic material is selected from the group consisting of: lithium niobate, lithium tantalate, potassium di-deuterium phosphate, β-barium borate, potassium titanium oxide phosphate, gallium arsenide, indium phosphide, transition metal dichalcogenides, and poled electro-optic polymers.

18. A system comprising:
a light source module configured to emit light;
a plurality of electric field sensors, each sensor comprising a light input portion configured to receive light emitted from the light source module and a light output portion configured to output light in response to the received light, each sensor comprising an electro-optic material arranged in a path of at least some of the received light, an optical property of the electro-optic material being variable depending on a local electric field strength at the sensor, and the electro-optic material being arranged in the sensor such that a property of the output light varies depending on the local electric field strength;
a light detection module arranged to receive the output light from the sensors; and
a processing module in communication with the light detection module, the processing module being programmed to determine a corresponding value for the electric field strength local to each of the sensors based on the detected output light from each respective sensor,
wherein the light emitted by the light source module comprises a pump wavelength and a plurality of probe wavelengths, the plurality of electric field sensors being responsive to one or more corresponding wavelengths of the plurality of probe wavelengths,
wherein each of the plurality of electric field sensors comprises an optical gain medium arranged in a path of at least some of the received light, the optical gain medium having an optical gain that vary depending on an amount of received pump light, and
wherein the electro-optic material is configured to transmit a variable portion of the pump wavelength to the optical gain medium depending on the electric field strength local to the respective electric field sensor, such that respective intensity of the output probe wavelengths are modified by the optical gain of the respective optical gain medium.

19. The system of claim 18, wherein the light emitted by the light source module comprises a plurality of wavelengths, the plurality of electric field sensors being responsive to one or more corresponding wavelengths of the plurality of wavelengths,
the light detection module being configured to separately detect light at each of the corresponding one or more of the plurality of wavelengths, and
the processing module being programmed to determine corresponding local electric field strength at each of the sensors based on the detected wavelengths of light corresponding to each sensor.

20. The system of claim 19, wherein the plurality of electric field sensors are arranged at different locations along a common optical path of the light from the light source module.

21. The system of claim 20, wherein the common optical path comprises an optical waveguide.

22. The system of claim 20, wherein each of the plurality of electric field sensors comprises a multiplexer and a demultiplexer.

23. The system of claim 19, further comprising an optical circulator optically coupled to the light source module, the plurality of electric field sensors, and the light detection module.

24. The system of claim 23, wherein the light source module emits optical pulses during operation and the processing module is programmed to correlate each of a plurality of detected optical pulses to a corresponding electric field sensor based on a respective arrival time of the detected optical pulse.

25. The system of claim 18, wherein the light emitted by the light source module comprises a plurality of wavelengths and the plurality of electric field sensors each have a respective resonant wavelength which vary depending on the electric field strength local to the respective electric field sensor.

26. The system of claim 18, wherein the electro-optic material is selected from the group consisting of: lithium niobate, lithium tantalate, potassium di-deuterium phosphate, (β-barium borate, potassium titanium oxide phosphate, gallium arsenide, indium phosphide, transition metal dichalcogenides, and poled electro-optic polymers.

* * * * *